United States Patent
Zhang et al.

(10) Patent No.: US 11,000,593 B2
(45) Date of Patent: May 11, 2021

(54) CELLULAR OR VIRAL MEMBRANE COATED NANOSTRUCTURES AND USES THEREOF

(71) Applicant: The Regents of the University of California, Oakland, CA (US)

(72) Inventors: Liangfang Zhang, San Diego, CA (US); Weiwei Gao, La Jolla, CA (US)

(73) Assignee: The Regents of the University of California, Oakland, CA (US)

( * ) Notice: Subject to any disclaimer, the term of this patent is extended or adjusted under 35 U.S.C. 154(b) by 361 days.

(21) Appl. No.: 16/067,950

(22) PCT Filed: Jan. 5, 2017

(86) PCT No.: PCT/US2017/012342
§ 371 (c)(1),
(2) Date: Jul. 3, 2018

(87) PCT Pub. No.: WO2017/120342
PCT Pub. Date: Jul. 13, 2017

(65) Prior Publication Data
US 2020/0268892 A1 Aug. 27, 2020

Related U.S. Application Data

(60) Provisional application No. 62/276,545, filed on Jan. 8, 2016.

(51) Int. Cl.
*A61K 9/16* (2006.01)
*A61K 47/34* (2017.01)
*A61K 9/00* (2006.01)
*A61K 35/39* (2015.01)
*C12N 5/071* (2010.01)

(52) U.S. Cl.
CPC ............ *A61K 47/34* (2013.01); *A61K 9/0092* (2013.01); *A61K 35/39* (2013.01); *C12N 5/0676* (2013.01); *C12N 2533/40* (2013.01)

(58) Field of Classification Search
None
See application file for complete search history.

(56) References Cited

U.S. PATENT DOCUMENTS

| | | |
|---|---|---|
| 2008/0241262 A1 | 10/2008 | Lee et al. |
| 2011/0201984 A1* | 8/2011 | Dubrow .................. A61L 31/10 602/54 |
| 2013/0337066 A1 | 12/2013 | Zhang et al. |

FOREIGN PATENT DOCUMENTS

| | | | |
|---|---|---|---|
| WO | 2013/052167 A2 | 4/2013 | |
| WO | 2015/021390 A2 | 2/2015 | |
| WO | WO-2015021390 A2 * | 2/2015 | ........... A61K 9/5176 |
| WO | 2015/187502 A1 | 12/2015 | |
| WO | 2016/109306 A1 | 7/2016 | |

OTHER PUBLICATIONS

PCT International Search Report and Written Opinion for PCT Application No. PCT/US2017/012342 dated Mar. 23, 2017 (9 pages).

* cited by examiner

*Primary Examiner* — Susan T Tran
(74) *Attorney, Agent, or Firm* — Eversheds Sutherland (US) LLP

(57) ABSTRACT

The present invention relates to viral or cellular membrane coated nanostructures. Nanostructure networks, nanoscaffolds and articles of manufacture comprising the nanostructure, and uses thereof, are also provided. The present invention also relates to methods for anchoring, attaching and/or growing a target cell. Target cells, constituent(s) of the target cells, target substances made by the target cells or culture medium of the target cells prepared by the present methods, and uses thereof, are also provided.

16 Claims, 4 Drawing Sheets

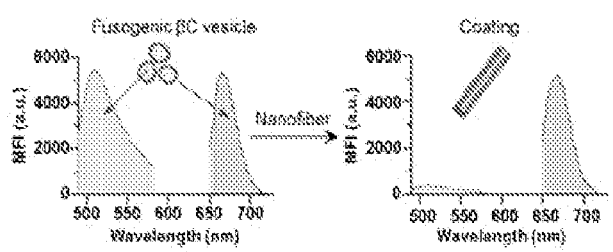 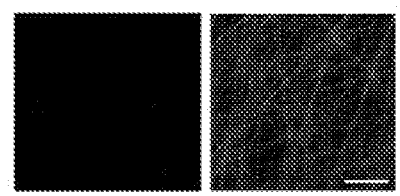
FIGURE 2A　　　　　　　　　　　FIGURE 2B
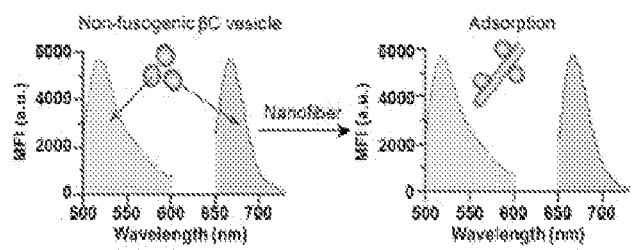 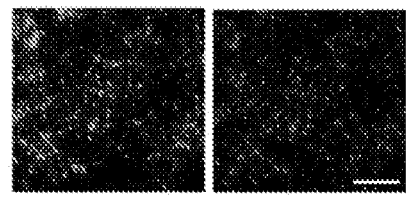
FIGURE 2C　　　　　　　　　　　FIGURE 2D

CELLULAR OR VIRAL MEMBRANE COATED NANOSTRUCTURES AND USES THEREOF

CROSS REFERENCE TO RELATED APPLICATIONS

This application claims the priority benefit of PCT/US2017/012342 filed on Jan. 5, 2017 which claims the benefit of U.S. Provisional Application No. 62/276,545, filed Jan. 8, 2016, the entire contents of which are hereby incorporated by reference herein.

STATEMENT REGARDING FEDERALLY SPONSORED RESEARCH

This invention was made with Government support under Grant No. R01DK095168 awarded by the National Institutes of Health and under Grant No. DMR-1505699 awarded by the National Science Foundation. The Government has certain rights in the invention.

FIELD OF THE INVENTION

The present invention relates to viral or cellular membrane coated nanostructures. Nanostructure networks, nanoscaffolds and articles of manufacture comprising the nanostructure, and uses thereof, are also provided. The present invention also relates to methods for anchoring, attaching and/or growing a target cell. Target cells, constituent(s) of the target cells, target substances made by the target cells or culture medium of the target cells prepared by the present methods, and uses thereof, are also provided.

BACKGROUND OF THE INVENTION

The key components for tissue engineering and cell delivery consist of cells, scaffolds, and growth-stimulating factors.[1,2] Among this triad, scaffolds provide a solid matrix for cell attachment and proliferation, while supplying physicochemical and/or bioactive cues to the residing cells.[3,4] The interactions between cells and scaffolds are of particular importance, which determine the survival and function of the cells.[5,6] Therefore, scaffolds, typically made of polymeric biomaterials such as polymeric nanofibers, are often modified with cell surface receptors to stimulate intracellular signaling, alter protein expression, and modulate cell function.[7,10] Common strategies to implement such surface modifications are chemical conjugation and physical absorption.[11-13] A variety of soluble receptors including intercellular adhesion molecules 1 (ICAM-1),[14] E-cadherin,[15] and Ephrin[16,17] have been conjugated onto synthetic scaffolds to enhance cell survival and function. To alleviate potential risk of protein denaturation by these chemical and physical processes, synthetic lipid bilayers have been successfully coated onto nanofiber scaffolds.[18,19] The lipid membranes not only shield the nanofibers from external environment but also provide a biomolecule-friendly medium to anchor cell surface receptors and preserve their integrity and functionality. While these bottom-up functionalization approaches are competent to present individual receptors or receptor combinations to cells seeded in a scaffold, they are generally inadequate to replicate the complex cell surface properties and functions critical for cell-cell interaction and cell proliferation in a scaffold.[20,21]

The use of cell membranes to cloak synthetic nanoparticles through a top-down fabrication method has emerged as a promising technique for nanomaterial surface functionalization.[22,23] Such cloaking technique bestows nanoparticles with complex cell surface properties and functions that are otherwise difficult to replicate. Currently, a variety of cell membrane-coated nanoparticle systems have been developed with unique features and functions, which involve different cell types (e.g., red blood cell, platelet, leukocyte, cancer cell and bacterium) and different synthetic nanoparticles (e.g., polymeric nanoparticle, gold nanoparticle, and silica nanoparticle)[24-27]. These biomimetic nanoparticles have demonstrated a wide range of biomedical applications including drug delivery, photodynamic therapy, detoxification, and vaccination.[28-31] However, the cell membrane cloaking technique has not been generalized from spherical nanoparticles to spidery nanofibers, which exhibit aspect ratios drastically different from nanoparticles.

Therefore, novel nanostructures that mimic or replicate the complex viral or cell surface properties and/or functions are needed. The present invention addresses this and the related needs in the art.

SUMMARY OF THE INVENTION

The invention provides viral or cellular membrane coated nanostructures and use thereof. Detailed descriptions of certain aspects of the composition and nanostructures are provided in WO2013/052167 and US Publication No. 20130337066, the entire contents of which are incorporated by reference herewith.

In one aspect, the invention provides for a nanostructure comprising: a) an inner core comprising a non-cellular or non-viral material; and b) an outer surface comprising a membrane derived from a cell or a membrane derived from a virus, wherein said nanostructure: 1) has a first dimension with a first dimensional parameter ranging from about 1 nm to about 10 µm and a second dimension with a second dimensional parameter of at least about 11 µm; and/or 2) has a first dimension with a first dimensional parameter ranging from about 1 nm to about 10 µm, a second dimension with a second dimensional parameter, and a ratio between said second dimensional parameter and said first dimensional parameter of at least about 2. Nanostructure networks, nanoscaffolds and articles of manufacture comprising the nanostructure are also provided. Uses of the nanostructures, nanostructure networks, nanoscaffolds and articles of manufacture are further provided.

In another aspect, the invention provides a method for anchoring, attaching and/or growing a target cell, which method comprises contacting a target cell with a nanostructure under conditions that allow said target cell to anchor on or attach to said nanostructure and/or grow, wherein said nanostructure comprises an inner core comprising a non-cellular material and an outer surface comprising a membrane derived from a source cell and/or virus, and wherein said membrane derived from said source cell and/or virus allows said target cell to anchor on or attach to said nanostructure. Target cells, constituent(s) of the target cells, target substances made by the target cells or culture medium of the target cells prepared by the present methods are also provided. Uses of the target cells, constituent(s) of the target cells, target substances made by the target cells or culture medium of the target cells are further provided.

In some embodiments, the present nanostructures, nanostructure networks, nanoscaffolds and articles of manufacture, medicament delivery systems, pharmaceutical compositions and methods, can be used to deliver the exemplary medications listed in the Orange Book: Approved Drug Products with Therapeutic Equivalence Evaluations (Current through March 2012) published by the U.S. Food and Drug Administration, the exemplary medications listed in *The Merck Index* (a U.S. publication, the printed 14th Edition, Whitehouse Station, N.J., USA) and its online version (The Merck Index Online[SM], Last Loaded on Web: Tuesday, May 1, 2012), and the exemplary medications listed in Biologics Products & Establishments published by the U.S. Food and Drug Administration, and can be used to treat or prevent the corresponding diseases and disorders.

In some aspects, the present disclosure relates to U.S. application Ser. No. 13/827,906, filed Mar. 14, 2013, International Application No. PCT/US2012/039411, filed May 24, 2012 and published as WO 2013/052167 A2 and U.S. provisional application Ser. No. 61/492,626, filed Jun. 2, 2011. The contents of the above applications are incorporated by reference in their entireties.

BRIEF DESCRIPTION OF THE DRAWINGS

Those of skill in the art will understand that the drawings, described below, are for illustrative purposes only. The drawings are not intended to limit the scope of the present teachings in any way.

FIG. 1A shows a schematic illustration showing the preparation of CM-fibers. The process can be divided into three steps: deriving membrane vesicles from beta cells (βC vesicles), fabricating uncoated nanofibers (Un-fibers) via an electrospinning method, and fusing the βC vesicles onto the surface of the Un-fibers. FIG. 1B shows a representative SEM image depicting the fibrous morphology of the resulting CM-fibers (scale bar, 1 μm). FIG. 1C shows the size and size distribution of the CM-fibers.

FIGS. 2A-2D. FIGS. 2A and 2B confirm the fusion of the βC vesicles onto the nanofibers. The βC vesicles were labeled with two distinct fluorescent dyes: DiD (red) in the cell membrane and calcein-AM (green) in the aqueous compartment of the vesicles. FIG. 2A shows a fluorescence emission spectra of the βC vesicles (left panel) and CM-fibers (right panel). FIG. 2B shows fluorescent images of the CM-fibers in the green channel (left panel) and the red channel (right panel). FIGS. 2C and 2D show βC vesicles (labeled with DiD, red) that were pre-coated onto PLGA polymeric nanoparticles (labeled with Alexa 488, green) to passivate their fusion ability. FIG. 2C shows fluorescence emission spectra of the non-fusogenic βC vesicles (left panel) and their mixture with the nanofibers (right panel). FIG. 2D shows fluorescent images of the nanofibers after incubation with the non-fusogenic βC vesicles in the green channel (left panel) and the red channel (right panel). Scale bars, 25 μm.

FIG. 3A shows static water contact angle measurements of Un-fibers and CM-fibers. FIG. 3B shows the weight percentage of protein content on Un-fibers and CM-fibers. Error bars represent the standard deviation of three measurements. FIG. 3C shows the SDS-PAGE analysis of proteins present on the βC vesicles and the CM-fibers. The samples were run at equal protein content and stained with Coomassie Blue. FIG. 3D shows western blotting analysis of cell membrane markers, Na+K+/ATPase and E-cadherin, present on the βC vesicles and the CM-fibers. FIG. 3E shows a representative fluorescent image of CM-fibers after immunostaining of E-cadherin (scale bar, 25 μm).

FIG. 4A shows fluorescent images of MIN6 cells cultured on bare glass cover slip, Un-fibers, or CM-fibers. The cells were stained with calcein-AM/PI assay prior to imaging. FIG. 4B shows the proliferation rate of the cells quantified on day 1, day 4 and day 7. FIG. 4C shows the size distribution of MIN6 cell clusters on day 7. FIG. 4D shows the insulin secretion index of MIN6 cells cultured on the three different substrates.

DETAILED DESCRIPTION OF THE INVENTION

Figure 1A:
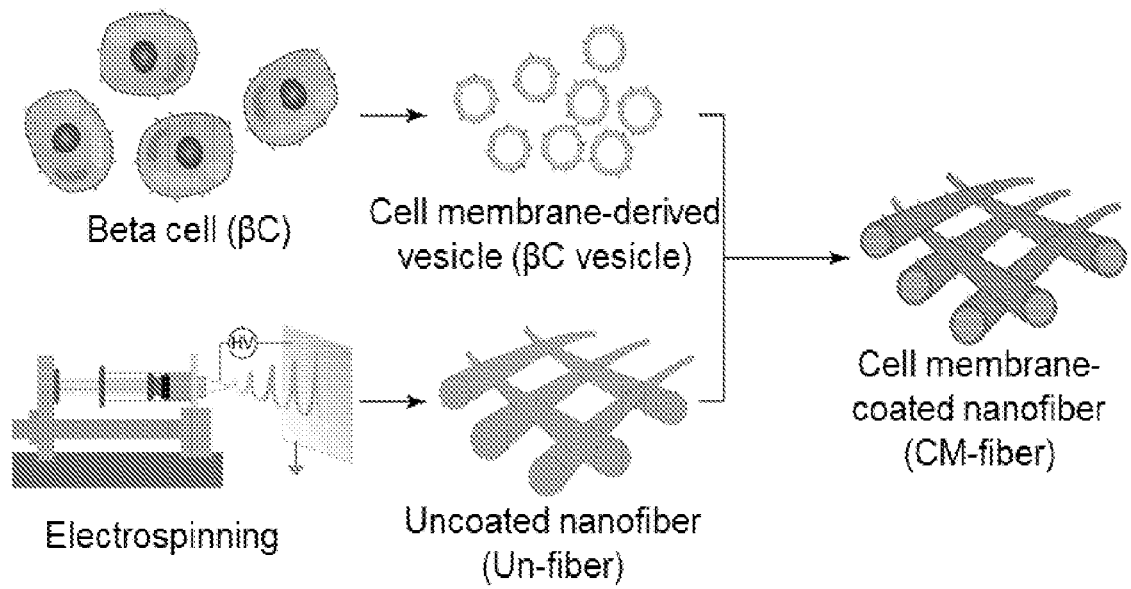
FIGS. 1A-1C illustrate the preparation and characterization of cell membrane-coated nanofibers (CM-fibers).

The practice of the present invention will employ, unless otherwise indicated, conventional techniques of nanotechnology, nano-engineering, molecular biology (including recombinant techniques), microbiology, cell biology, biochemistry, immunology, and pharmacology, which are within the skill of the art. Such techniques are explained fully in the literature, such as, Molecular Cloning: A Laboratory Manual, $2^{nd}$ ed. (Sambrook et al., 1989); Oligonucleotide Synthesis (M. J. Gait, ed., 1984); Animal Cell Culture (R. I. Freshney, ed., 1987); Methods in Enzymology (Academic Press, Inc.); Current Protocols in Molecular Biology (F. M. Ausubel et al., eds., 1987, and periodic updates); PCR: The Polymerase Chain Reaction (Mullis et al., eds., 1994); Remington, The Science and Practice of Pharmacy, $20^{th}$ ed., (Lippincott, Williams & Wilkins 2003), and Remington, The Science and Practice of Pharmacy, $22^{th}$ ed., (Pharmaceutical Press and Philadelphia College of Pharmacy at University of the Sciences 2012).

Unless defined otherwise, all technical and scientific terms used herein have the same meaning as is commonly understood by one of ordinary skill in the art to which this invention belongs. All patents, applications, published applications and other publications referred to herein are incorporated by reference in their entireties. If a definition set forth in this section is contrary to or otherwise inconsistent with a definition set forth in the patents, applications, published applications and other publications that are herein incorporated by reference, the definition set forth in this section prevails over the definition that is incorporated herein by reference.

A. DEFINITIONS

To facilitate understanding of the invention, a number of terms and abbreviations as used herein are defined below as follows:

When introducing elements of the present invention or the preferred embodiment(s) thereof, the articles "a", "an", "the" and "said" are intended to mean that there are one or more of the elements. The terms "comprising", "including" and "having" are intended to be inclusive and mean that there may be additional elements other than the listed elements.

The term "and/or" when used in a list of two or more items, means that any one of the listed items can be employed by itself or in combination with any one or more of the listed items. For example, the expression "A and/or B" is intended to mean either or both of A and B, i.e. A alone, B alone or A and B in combination. The expression "A, B and/or C" is intended to mean A alone, B alone, C alone, A and B in combination, A and C in combination, B and C in combination or A, B, and C in combination.

Membrane: The term "membrane" as used herein refers to a biological membrane enclosing or separating structure acting as a selective barrier, within or around a cell or an emergent viral particle. The membrane is selectively permeable to ions and organic molecules and controls the movement of substances in and out of cells and/or viruses. The membrane comprises a phospholipid uni- or bilayer, and optionally associated proteins and carbohydrates. As used herein, the membrane refers to a membrane obtained from a naturally occurring biological membrane of a cell/virus or cellular organelles, or one derived therefrom. As used herein, the term "naturally occurring" refers to one existing in nature. As used herein, the term "derived therefrom" refers to any subsequent modification of the natural membrane, such as isolating the membrane, creating portions or fragments of the membrane, removing and/or adding certain components, such as lipid, protein or carbohydrates, from or into the membrane taken from a cell/virus or a cellular organelle. A membrane can be derived from a naturally occurring membrane by any suitable methods. For example, a membrane can be prepared or isolated from a cell or a virus and the prepared or isolated membrane can be combined with other substances or materials to form a derived membrane. In another example, a cell or virus can be recombinantly engineered to produce "non-natural" substances that are incorporated into its membrane in vivo, and the cellular or viral membrane can be prepared or isolated from the cell or the virus to form a derived membrane.

In various embodiments, the membrane covering a nanostructure can be further modified to be saturated or unsaturated with other lipid components, such as cholesterol, free fatty acids, and phospholipids, also can include endogenous or added proteins and carbohydrates, such as cellular surface antigens. In such cases, an excess amount of the other lipid components can be added to the membrane wall which will shed until the concentration in the membrane wall reaches equilibrium, which can be dependent upon the nanostructure environment. Membranes may also comprise other agents that may or may not increase an activity of the nanostructure. In other examples, functional groups such as antibodies and aptamers can be added to the outer surface of the membrane to enhance site targeting, such as to cell surface epitopes. The membrane of the nanostructure can also comprise particles that can be biodegradable, cationic nanoparticles including, but not limited to, gold, silver, and synthetic nanoparticles.

Synthetic or artificial membrane: As used herein, the term "synthetic membrane" or "artificial membrane" refers to a man-made membrane that is produced from organic material, such as polymers and liquids, as well as inorganic materials. A wide variety of synthetic membranes are well known in the art.

Nanostructure: The term "nanostructure" as used herein refers to a structure, e.g., a nanofiber, a nanotube, a nanowire, or a nanosheet, having at least one dimension (e.g., height, length, width, or diameter) of between about 1 nm and about 10 μm. A "nanostructure" can be a 1 D nanostructure or a 2 D nanostructure. A dimensional parameter of a second dimension and/or a third dimension may or may not be in a dimensional range (e.g., height, length, width, or diameter) between about 1 nm and about 10 μm. The term "nanostructure" includes, but is not necessarily limited to, a nanofiber, a nanotube, a nanowire, or a nanosheet and engineered features. The nanostructure and engineered features can have, for example, a regular or irregular shape. The nanostructure can be composed of inorganic, organic materials or other materials, and can alternatively be implemented with porous materials. The layer of nanostructures can be implemented with nanostructures in a monolayer or with a layer having agglomerations of nanostructures. In some embodiments, the nanostructure has an inner core covered by an outer surface comprising a cellular or viral derived membrane. The invention contemplates any nanostructures now known and later developed that can be coated with the membranes described herein.

Pharmaceutically active: The term "pharmaceutically active" as used herein refers to the beneficial biological activity of a substance on living matter and, in particular, on cells and tissues of the human body. A "pharmaceutically active agent" or "drug" is a substance that is pharmaceutically active and a "pharmaceutically active ingredient" (API) is the pharmaceutically active substance in a drug.

Pharmaceutically acceptable: The term "pharmaceutically acceptable" as used herein means approved by a regulatory agency of the Federal or a state government or listed in the U.S. Pharmacopoeia, other generally recognized pharmacopoeia in addition to other formulations that are safe for use in animals, and more particularly in humans and/or non-human mammals.

Pharmaceutically acceptable salt: The term "pharmaceutically acceptable salt" as used herein refers to acid addition salts or base addition salts of nanostructures or compounds in the present disclosure. A pharmaceutically acceptable salt is any salt which retains the activity of the parent nanostructure or compound and does not impart any deleterious or undesirable effect on a subject to whom it is administered and in the context in which it is administered. Pharmaceutically acceptable salts may be derived from amino acids including, but not limited to, cysteine. Methods for producing compounds as salts are known to those of skill in the art (see, for example, Stahl et al., Handbook of Pharmaceutical Salts: Properties, Selection, and Use, Wiley-VCH; Verlag Helvetica Chimica Acta, Zurich, 2002; Berge et al., J Pharm. Sci. 66:1, 1977). In some embodiments, a "pharmaceutically acceptable salt" is intended to mean a salt of a free acid or base of a nanostructure or compound represented herein that is non-toxic, biologically tolerable, or otherwise biologically suitable for administration to the subject. See, generally, Berge, et al., J. Pharm. Sci., 1977, 66, 1-19. Preferred pharmaceutically acceptable salts are those that are pharmacologically effective and suitable for contact with the tissues of subjects without undue toxicity, irritation, or allergic response. A nanostructure or compound described herein may possess a sufficiently acidic group, a sufficiently basic group, both types of functional groups, or more than one of each type, and accordingly react with a number of inorganic or organic bases, and inorganic and organic acids, to form a pharmaceutically acceptable salt.

Examples of pharmaceutically acceptable salts include sulfates, pyrosul fates, bisulfates, sulfites, bisulfites, phosphates, monohydrogen-phosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methylbenzoates, dinitrobenzoates, hydroxybenzoates, methoxybenzoates, phthalates, sulfonates, methylsulfonates, propylsulfonates, besylates, xylenesulfonates, naphthalene-1-sulfonates, naphthalene-2-sulfonates, phenylacetates, phenylpropionates, phenylbutyrates, citrates, lactates, [gamma]-hydroxybutyrates, glycolates, tartrates, and mandelates.

Pharmaceutically acceptable carrier: The term "pharmaceutically acceptable carrier" as used herein refers to an excipient, diluent, preservative, solubilizer, emulsifier, adjuvant, and/or vehicle with which a nanostructure or compound is administered. Such carriers may be sterile liquids, such as water and oils, including those of petroleum, animal, vegetable or synthetic origin, such as peanut oil, soybean oil, mineral oil, sesame oil and the like, polyethylene glycols, glycerine, propylene glycol or other synthetic solvents. Antibacterial agents such as benzyl alcohol or methyl parabens; antioxidants such as ascorbic acid or sodium bisulfite; chelating agents such as ethylenediaminetetraacetic acid; and agents for the adjustment of tonicity such as sodium chloride or dextrose may also be a carrier. Methods for producing compositions in combination with carriers are known to those of skill in the art. In some embodiments, the language "pharmaceutically acceptable carrier" is intended to include any and all solvents, dispersion media, coatings, isotonic and absorption delaying agents, and the like, compatible with pharmaceutical administration. The use of such media and agents for pharmaceutically active substances is well known in the art. See, e.g., Remington, The Science and Practice of Pharmacy. 20'" ed., (Lippincott, Williams & Wilkins 2003). Except insofar as any conventional media or agent is incompatible with the active compound, such use in the compositions is contemplated.

Phospholipid: The term "phospholipid", as used herein, refers to any of numerous lipids contain a diglyceride, a phosphate group, and a simple organic molecule such as choline. Examples of phospholipids include, but are not limited to, Phosphatide acid (phosphatidate) (PA), Phosphatidylethanolamine (cephalin) (PE), Phosphatidylcholine (lecithin) (PC), Phosphatidylserine (PS), and Phosphoinositides which include, but are not limited to, Phosphatidylinositol (PI), Phosphatidylinositol phosphate (PIP), Phosphatidylinositol bisphosphate (PIP2) and Phosphatidylinositol triphosphate (P1P3). Additional examples of PC include DDPC, DLPC, DMPC, DPPC, DSPC, DOPC, POPC, DRPC, and DEPC as defined in the art.

Therapeutically Effective Amount: As used herein, the term "therapeutically effective amount" refers to those amounts that, when administered to a particular subject in view of the nature and severity of that subject's disease or condition, will have a desired therapeutic effect, e.g., an amount which will cure, prevent, inhibit, or at least partially arrest or partially prevent a target disease or condition. In some embodiments, the term "therapeutically effective amount" or "effective amount" refers to an amount of a therapeutic agent that when administered alone or in combination with an additional therapeutic agent to a cell, tissue, or subject is effective to prevent or ameliorate the disease or condition, or the progression of the disease or condition. A therapeutically effective dose further refers to that amount of the therapeutic agent sufficient to result in amelioration of symptoms, e.g., treatment, healing, prevention or amelioration of the relevant medical condition, or an increase in rate of treatment, healing, prevention or amelioration of such conditions. When applied to an individual active ingredient administered alone, a therapeutically effective dose refers to that ingredient alone. When applied to a combination, a therapeutically effective dose refers to combined amounts of the active ingredients that result in the therapeutic effect, whether administered in combination, serially or simultaneously.

"Treating" or "treatment" or "alleviation" refers to therapeutic treatment wherein the object is to slow down (lessen) if not cure the targeted pathologic condition or disorder or prevent recurrence of the condition. A subject is successfully "treated" if, after receiving a therapeutic amount of a therapeutic agent, the subject shows observable and/or measurable reduction in or absence of one or more signs and symptoms of the particular disease. Reduction of the signs or symptoms of a disease may also be felt by the patient. A patient is also considered treated if the patient experiences stable disease. In some embodiments, treatment with a therapeutic agent is effective to result in the patients being disease-free 3 months after treatment, preferably 6 months, more preferably one year, even more preferably 2 or more years post treatment. These parameters for assessing successful treatment and improvement in the disease are readily measurable by routine procedures familiar to a physician of appropriate skill in the art.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

The term "combination" refers to either a fixed combination in one dosage unit form, or a kit of parts for the combined administration where a nanostructure or compound and a combination partner (e.g., another drug as explained below, also referred to as "therapeutic agent" or "co-agent") may be administered independently at the same time or separately within time intervals, especially where these time intervals allow that the combination partners show a cooperative, e.g., synergistic effect. The terms "co-administration" or "combined administration" or the like as utilized herein are meant to encompass administration of the selected combination partner to a single subject in need thereof (e.g., a patient), and are intended to include treatment regimens in which the agents are not necessarily administered by the same route of administration or at the same time. The term "pharmaceutical combination" as used herein means a product that results from the mixing or combining of more than one active ingredient and includes both fixed and non-fixed combinations of the active ingredients. The term "fixed combination" means that the active ingredients, e.g., a nanostructure or compound and a combination partner, are both administered to a patient simultaneously in the form of a single entity or dosage. The term "non-fixed combination" means that the active ingredients, e.g., a nanostructure or compound and a combination partner, are both administered to a patient as separate entities either simultaneously, concurrently or sequentially with no specific time limits, wherein such administration provides therapeutically effective levels of the two moieties or compounds in the body of the patient. The latter also applies to cocktail therapy, e.g., the administration of three or more active ingredients.

It is understood that aspects and embodiments of the invention described herein include "consisting" and/or "consisting essentially of" aspects and embodiments.

Throughout this disclosure, various aspects of this invention are presented in a range format. It should be understood that the description in range format is merely for convenience and brevity and should not be construed as an inflexible limitation on the scope of the invention. Accordingly, the description of a range should be considered to have specifically disclosed all the possible sub-ranges as well as individual numerical values within that range. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein, a subject in need refers to an animal, a non-human mammal or a human. As used herein, "animals" include a pet, a farm animal, an economic animal, a sport animal and an experimental animal, such as a cat, a dog, a horse, a cow, an ox, a pig, a donkey, a sheep, a lamb, a goat, a mouse, a rabbit, a chicken, a duck, a goose, a primate, including a monkey and a chimpanzee.

The term "about" as used herein refers to the usual error range for the respective value readily known to the skilled person in this technical field. Reference to "about" a value or parameter herein includes (and describes) embodiments that are directed to that value or parameter per se. For example, description referring to "about X" includes description of "X". If the usual error range is not readily discernable to the skill person, about refers to +/−5% of the stated value.

The terms "polypeptide", "oligopeptide", "peptide" and "protein" are used interchangeably herein to refer to polymers of amino acids of any length, e.g., at least 5, 6, 7, 8, 9, 10, 20, 30, 40, 50, 100, 200, 300, 400, 500, 1,000 or more amino acids. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared.

As used herein, the term "antigen" refers to a target molecule that is specifically bound by an antibody through its antigen recognition site. The antigen may be monovalent or polyvalent, i.e., it may have one or more epitopes recognized by one or more antibodies. Examples of kinds of antigens that can be recognized by antibodies include polypeptides, oligosaccharides, glycoproteins, polynucleotides, lipids, etc.

As used herein, the term "epitope" refers to a peptide sequence of at least about 3 to 5, preferably about 5 to 10 or 15, and not more than about 1,000 amino acids (or any integer there between), which define a sequence that by itself or as part of a larger sequence, binds to an antibody generated in response to such sequence. There is no critical upper limit to the length of the fragment, which may, for example, comprise nearly the full-length of the antigen sequence, or even a fusion protein comprising two or more epitopes from the target antigen. An epitope for use in the subject invention is not limited to a peptide having the exact sequence of the portion of the parent protein from which it is derived, but also encompasses sequences identical to the native sequence, as well as modifications to the native sequence, such as deletions, additions and substitutions (conservative in nature).

The term "antibody" herein is used in the broadest sense and includes polyclonal and monoclonal antibodies, including intact antibodies and functional (antigen-binding) antibody fragments, including fragment antigen binding (Fab) fragments, F(ab')$_2$ fragments, Fab' fragments, Fv fragments, recombinant IgG (rIgG) fragments, single chain antibody fragments, including single chain variable fragments (scFv), and single domain antibodies (e.g., sdAb, sdFv, nanobody) fragments. The term encompasses genetically engineered and/or otherwise modified forms of immunoglobulins, such as intrabodies, peptibodies, chimeric antibodies, fully human antibodies, humanized antibodies, and heteroconjugate antibodies, multispecific, e.g., bispecific, antibodies, diabodies, triabodies, and tetrabodies, tandem di-scFv, tandem tri-scFv. Unless otherwise stated, the term "antibody" should be understood to encompass functional antibody fragments thereof. The term also encompasses intact or full-length antibodies, including antibodies of any class or sub-class, including IgG and sub-classes thereof, IgM, IgE, IgA, and IgD.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, 667, ε, γ, and μ, respectively.

As used herein, the term "epitope" or "antigenic determinant" refers to a site on an antigen to which B and/or T cells respond or a site on a molecule against which an antibody will be produced and/or to which an antibody will bind. For example, an epitope can be recognized by an antibody defining the epitope. An epitope can be either a "linear epitope" (where a primary amino acid primary sequence comprises the epitope; typically at least 3 contiguous amino acid residues, and more usually, at least 5, at least 6, at least 7, and up to about 8 to about 10 amino acids in a unique sequence) or a "conformational epitope" (an epitope wherein the primary, contiguous amino acid sequence is not the sole defining component of the epitope). A conformational epitope may comprise an increased number of amino acids relative to a linear epitope, as this conformational epitope recognizes a three-dimensional structure of the peptide or protein. For example, when a protein molecule folds to form a three dimensional structure, certain amino acids and/or the polypeptide backbone forming the conformational epitope become juxtaposed enabling the antibody to recognize the epitope. Methods of determining conformation of epitopes include but are not limited to, for example, x-ray crystallography, two-dimensional nuclear magnetic resonance spectroscopy and site-directed spin labeling and electron paramagnetic resonance spectroscopy. See, for example, Epitope Mapping Protocols in Methods in Molecular Biology, Vol. 66, Glenn E. Morris, Ed. (1996), the disclosure of which is incorporated in its entirety herein by reference.

Among the provided antibodies are antibody fragments. An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments. In particular embodiments, the antibodies are single-chain antibody fragments comprising a variable heavy chain region and/or a variable light chain region, such as scFvs.

Single-domain antibodies are antibody fragments comprising all or a portion of the heavy chain variable domain or all or a portion of the light chain variable domain of an antibody. In certain embodiments, a single-domain antibody is a camelid single-domain antibody.

Antibody fragments can be made by various techniques, including but not limited to proteolytic digestion of an intact antibody as well as production by recombinant host cells. In some embodiments, the antibodies are recombinantly-produced fragments, such as fragments comprising arrangements that do not occur naturally, such as those with two or more antibody regions or chains joined by synthetic linkers, e.g., peptide linkers, and/or that are may not be produced by enzyme digestion of a naturally-occurring intact antibody.

A "humanized" antibody is an antibody in which all or substantially all CDR amino acid residues are derived from non-human CDRs and all or substantially all FR amino acid residues are derived from human FRs. The term "chimeric" antibody refers to an antibody in which a portion of the heavy and/or light chain is derived from a particular source or species, while the remainder of the heavy and/or light chain is derived from a different source or species.

Among the provided antibodies are monoclonal antibodies, including monoclonal antibody fragments. The term "monoclonal antibody" as used herein refers to an antibody obtained from or within a population of substantially homogeneous antibodies, i.e., the individual antibodies comprising the population are identical, except for possible variants containing naturally occurring mutations or arising during production of a monoclonal antibody preparation, such variants generally being present in minor amounts. In contrast to polyclonal antibody preparations, which typically include different antibodies directed against different epitopes, each monoclonal antibody of a monoclonal antibody preparation is directed against a single epitope on an antigen. The term is not to be construed as requiring production of the antibody by any particular method. A monoclonal antibody may be made by a variety of techniques, including but not limited to generation from a hybridoma, recombinant DNA methods, phage-display and other antibody display methods.

As used herein, the term "specific binding" refers to the specificity of a binding reagent, e.g., an antibody, such that it preferentially binds to a target antigen. Recognition by a binding reagent or an antibody of a particular target in the presence of other potential interfering substances is one characteristic of such binding. Preferably, binding reagents, antibodies or antibody fragments that are specific for or bind specifically to a target antigen bind to the target antigen with higher affinity than binding to other non-target substances. Also preferably, binding reagents, antibodies or antibody fragments that are specific for or bind specifically to a target antigen avoid binding to a significant percentage of non-target substances, e.g., non-target substances present in a testing sample. In some embodiments, binding reagents, antibodies or antibody fragments of the present disclosure avoid binding greater than about 90% of non-target substances, although higher percentages are clearly contemplated and preferred. For example, binding reagents, antibodies or antibody fragments of the present disclosure avoid binding about 91%, about 92%, about 93%, about 94%, about 95%, about 96%, about 97%, about 98%, about 99%, and about 99% or more of non-target substances. In other embodiments, binding reagents, antibodies or antibody fragments of the present disclosure avoid binding greater than about 10%, 20%, 30%, 40%, 50%, 60%, or 70%, or greater than about 75%, or greater than about 80%, or greater than about 85% of non-target substances.

An "immunoconjugate" is an antibody conjugated to one or more heterologous molecule(s), including but not limited to a gold particle, a fluorescent dye or particle, quantum dots, and latex or any other labels, for example, for use in ELISA or lateral flow assays. In some embodiments, the antibody is or is part of an immunoconjugate, in which the antibody is conjugated to one or more heterologous molecule(s).

Conjugates of an antibody and one or more heterologous molecule(s) may be made using any of a number of known protein coupling agents, e.g., linkers, (see Vitetta et al., *Science* 238:1098 (1987)), WO94/11026. The linker may be a "cleavable linker," such as acid-labile linkers, peptidase-sensitive linkers, photolabile linkers, dimethyl linkers, and disulfide-containing linkers (Chari et al., *Cancer Res.* 52:127-131 (1992); U.S. Pat. No. 5,208,020).

An "isolated" polypeptide, e.g., isolated antibody, is one which has been separated from a component of its natural environment. In some embodiments, a polypeptide, e.g., an antibody, is purified to greater than 10%, 20%, 30%, 40%, 50%, 60%, 70%, 80%, 90%, 91%, 92%, 93%, 94%, 95%, 96%, 97%, 98%, 99%, 99.9%, 99.99%, 99.999%, or more purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of polypeptide, e.g., antibody, purity, see, e.g., Flatman et al., *J. Chromatogr. B* 848:79-87 (2007).

The terms "polynucleotide," "oligonucleotide," "nucleic acid" and "nucleic acid molecule" are used interchangeably herein to refer to a polymeric form of nucleotides of any length, e.g., at least 8, 9, 10, 20, 30, 40, 50, 100, 200, 300, 400, 500, 1,000 or more nucleotides, and may comprise ribonucleotides, deoxyribonucleotides, analogs thereof, or mixtures thereof. This term refers only to the primary structure of the molecule. Thus, the term includes triple-, double- and single-stranded deoxyribonucleic acid ("DNA"), as well as triple-, double- and single-stranded ribonucleic acid ("RNA"). It also includes modified, for example by alkylation, and/or by capping, and unmodified forms of the polynucleotide. More particularly, the terms "polynucleotide," "oligonucleotide," "nucleic acid" and "nucleic acid molecule" include polydeoxyribonucleotides (containing 2-deoxy-D-ribose), polyribonucleotides (containing D-ribose), including tRNA, rRNA, hRNA, and mRNA, whether spliced or unspliced, any other type of polynucleotide which is an N- or C-glycoside of a purine or pyrimidine base, and other polymers containing normucleotidic backbones, for example, polyamide (e.g., peptide nucleic acids ("PNAs")) and polymorpholino (commercially available from the Anti-Virals, Inc., Corvallis, Oreg., as Neugene) polymers, and other synthetic sequence-specific nucleic acid polymers providing that the polymers contain nucleobases in a configuration which allows for base pairing and base stacking, such as is found in DNA and RNA. Thus, these terms include, for example, 3'-deoxy-2',5'-DNA, oligodeoxyribonucleotide N3' to P5' phosphoramidates, 2'-O-alkyl-substituted RNA, hybrids between DNA and RNA or between PNAs and DNA or RNA, and also include known types of modifications, for example, labels, alkylation, "caps," substitution of one or more of the nucleotides with an analog, internucleotide modifications such as, for example, those with uncharged linkages (e.g., methyl phosphonates, phosphotriesters, phosphoramidates, carbamates, etc.), with negatively charged linkages (e.g., phosphorothioates, phosphorodithioates, etc.), and with positively charged linkages (e.g., aminoalkylphosphoramidates, aminoalkylphosphotriesters), those containing pendant moieties, such as, for example, proteins (including enzymes (e.g. nucleases), toxins, antibodies, signal peptides, poly-L-lysine, etc.), those with intercalators (e.g., acridine, psoralen, etc.), those containing chelates (of, e.g., metals, radioactive metals, boron, oxidative metals, etc.), those containing alkylators, those with modified linkages (e.g., alpha anomeric nucleic acids, etc.), as well as unmodified forms of the polynucleotide or oligonucleotide.

It will be appreciated that, as used herein, the terms "nucleoside" and "nucleotide" will include those moieties which contain not only the known purine and pyrimidine bases, but also other heterocyclic bases which have been modified. Such modifications include methylated purines or pyrimidines, acylated purines or pyrimidines, or other heterocycles. Modified nucleosides or nucleotides can also include modifications on the sugar moiety, e.g., wherein one or more of the hydroxyl groups are replaced with halogen, aliphatic groups, or are functionalized as ethers, amines, or the like. The term "nucleotidic unit" is intended to encompass nucleosides and nucleotides.

"Nucleic acid probe" and "probe" are used interchangeably and refer to a structure comprising a polynucleotide, as defined above, that contains a nucleic acid sequence that can bind to a corresponding target. The polynucleotide regions of probes may be composed of DNA, and/or RNA, and/or synthetic nucleotide analogs.

As used herein, "complementary or matched" means that two nucleic acid sequences have at least 50% sequence identity. Preferably, the two nucleic acid sequences have at least 60%, 70%, 80%, 90%, 95%, 96%, 97%, 98%, 99% or 100% of sequence identity. "Complementary or matched" also means that two nucleic acid sequences can hybridize under low, middle and/or high stringency condition(s).

As used herein, "substantially complementary or substantially matched" means that two nucleic acid sequences have at least 90% sequence identity. Preferably, the two nucleic acid sequences have at least 95%, 96%, 97%, 98%, 99% or 100% of sequence identity. Alternatively, "substantially complementary or substantially matched" means that two nucleic acid sequences can hybridize under high stringency condition(s).

In general, the stability of a hybrid is a function of the ion concentration and temperature. Typically, a hybridization reaction is performed under conditions of lower stringency, followed by washes of varying, but higher, stringency. Moderately stringent hybridization refers to conditions that permit a nucleic acid molecule such as a probe to bind a complementary nucleic acid molecule. The hybridized nucleic acid molecules generally have at least 60% identity, including for example at least any of 70%, 75%, 80%, 85%, 90%, or 95% identity. Moderately stringent conditions are conditions equivalent to hybridization in 50% formamide, 5×Denhardt's solution, 5×SSPE, 0.2% SDS at 42° C., followed by washing in 0.2×SSPE, 0.2% SDS, at 42° C. High stringency conditions can be provided, for example, by hybridization in 50% formamide, 5×Denhardt's solution, 5×SSPE, 0.2% SDS at 42° C., followed by washing in 0.1×SSPE, and 0.1% SDS at 65° C. Low stringency hybridization refers to conditions equivalent to hybridization in 10% formamide, 5×Denhardt's solution, 6×SSPE, 0.2% SDS at 22° C., followed by washing in 1×SSPE, 0.2% SDS, at 37° C. Denhardt's solution contains 1% Ficoll, 1% polyvinylpyrolidone, and 1% bovine serum albumin (BSA). 20×SSPE (sodium chloride, sodium phosphate, ethylene diamide tetraacetic acid (EDTA)) contains 3M sodium chloride, 0.2M sodium phosphate, and 0.025 M EDTA. Other suitable moderate stringency and high stringency hybridization buffers and conditions are well known to those of skill in the art and are described, for example, in Sambrook et al., Molecular Cloning: A Laboratory Manual, 2nd ed., Cold Spring Harbor Press, Plainview, N.Y. (1989); and Ausubel et al., Short Protocols in Molecular Biology, 4th ed., John Wiley & Sons (1999).

Alternatively, substantial complementarity exists when an RNA or DNA strand will hybridize under selective hybridization conditions to its complement. Typically, selective hybridization will occur when there is at least about 65% complementary over a stretch of at least 14 to 25 nucleotides, preferably at least about 75%, more preferably at least about 90% complementary. See Kanehisa (1984) *Nucleic Acids Res.* 12:203-215.

The terms "homologous", "substantially homologous", and "substantial homology" as used herein denote a sequence of amino acids having at least 50%, 60%, 70%, 80% or 90% identity wherein one sequence is compared to a reference sequence of amino acids. The percentage of sequence identity or homology is calculated by comparing one to another when aligned to corresponding portions of the reference sequence.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location. In some embodiments, a nucleic acid is purified to greater than 10%, 20%, 30%, 40%, 50%, 60%, 70%, 80%, 90%, 91%, 92%, 93%, 94%, 95%, 96%, 97%, 98%, 99%, 99.9%, 99.99%, 99.999%, or more purity.

An "individual" or "subject" includes a mammal. Mammals include, but are not limited to, domesticated animals (e.g., cows, sheep, cats, dogs, and horses), primates (e.g., humans and non-human primates such as monkeys), rabbits, and rodents (e.g., mice and rats). An "individual" or "subject" may include birds such as chickens, vertebrates such as fish and mammals such as mice, rats, rabbits, cats, dogs, pigs, cows, ox, sheep, goats, horses, monkeys and other non-human primates. In certain embodiments, the individual or subject is a human.

As used herein, a "sample" can be a solution, a suspension, liquid, powder, a paste, aqueous, non-aqueous or any combination thereof.

In some embodiments, the sample is a biological sample. A biological sample of the present disclosure encompasses a sample in the form of a solution, a suspension, a liquid, a powder, a paste, an aqueous sample, or a non-aqueous sample. As used herein, a "biological sample" includes any sample obtained from a living or viral (or prion) source or other source of macromolecules and biomolecules, and includes any cell type or tissue of a subject from which nucleic acid, protein and/or other macromolecule can be obtained. The biological sample can be a sample obtained directly from a biological source or a sample that is processed. For example, isolated nucleic acids that are amplified constitute a biological sample. Biological samples include, but are not limited to, body fluids, such as blood, plasma, serum, cerebrospinal fluid, synovial fluid, urine and sweat, tissue and organ samples from animals and plants and processed samples derived therefrom. In some embodiments, the sample can be derived from a tissue or a body fluid, for example, a connective, epithelium, muscle or nerve tissue; a tissue selected from the group consisting of brain, lung, liver, spleen, bone marrow, thymus, heart, lymph, blood, bone, cartilage, pancreas, kidney, gall bladder, stomach, intestine, testis, ovary, uterus, rectum, nervous system, gland, and internal blood vessels; or a body fluid selected from the group consisting of blood, urine, saliva, bone marrow, sperm, an ascitic fluid, and subfractions thereof, e.g., serum or plasma. Also included are soil and water samples and other environmental samples, viruses, bacteria, fungi, algae, protozoa and components thereof.

The terms "level" or "levels" are used to refer to the presence and/or amount of biomarkers, e.g., polypeptides and/or polynucleotides, and can be determined qualitatively or quantitatively. In some embodiments, a "qualitative" change in the biomarker level refers to the appearance or disappearance of a biomarker that is not detectable or is present in samples obtained from normal controls. In some embodiments, a "quantitative" change in the levels of one or more biomarker of the profile refers to a measurable increase or decrease in the biomarker levels when compared to a healthy control.

Other objects, advantages and features of the present invention will become apparent from the following specification taken in conjunction with the accompanying drawings.

B. CELLULAR OR VIRAL MEMBRANE COATED NANOSTRUCTURES AND USES THEREOF

In one aspect, the present invention provides for a nanostructure comprising: a) an inner core comprising a non-cellular or non-viral material; and b) an outer surface comprising a membrane derived from a cell or a membrane derived from a virus, wherein said nanostructure: 1) has a first dimension with a first dimensional parameter ranging from about 1 nm to about 10 μm and a second dimension with a second dimensional parameter of at least about 11 μm; and/or 2) has a first dimension with a first dimensional parameter ranging from about 1 nm to about 10 μm, a second dimension with a second dimensional parameter, and a ratio between said second dimensional parameter and said first dimensional parameter of at least about 2.

The inner core of the present nanostructure can comprise any suitable substance or an aggregate or a complex thereof. For example, the inner core can comprise an inorganic substance, an organic substance, or an aggregate or a complex thereof. In some embodiments, the inorganic substance comprises a superconducting substance, e.g., YBCO, a metallic substance, e.g., Ni, Pt, or Au, a semiconducting substance, e.g., Si, InP or GaN, an insulating substance, e.g., $SiO_2$ or $TiO_2$, an ion, e.g., a sodium, a potassium, a magnesium, a calcium, a chlorine, an iron, a copper, a zinc, a manganese, a cobalt, an iodine, a molybdenum, a vanadium, a nickel, a chromium, a fluorine, a silicon, a tin, a boron or an arsenic ion, or a coordination complex, e.g., a metal containing coordination complex.

In other embodiments, the organic substance is selected from an amino acid, a peptide, a protein, a nucleoside, a nucleotide, an oligonucleotide, a nucleic acid, e.g., DNA or RNA, a vitamin, a monosaccharide, an oligosaccharide, a carbohydrate, a lipid, or an aggregate or a complex thereof. Any suitable amino acids can be used. For example, a D- and a L-amino-acid can be used. In addition, any building blocks of naturally occurring peptides and proteins including Ala (A), Arg (R), Asn (N), Asp (D), Cys (C), Gln (Q), Glu (E), Gly (G), His (H), Ile (I), Leu (L), Lys (K), Met (M), Phe (F), Pro (P) Ser (S), Thr (T), Trp (W), Tyr (Y) and Val (V) can be used.

Any suitable proteins or peptides can be used. For example, enzymes, nutrient or storage proteins, contractile or motile proteins such as actins and myosins, structural proteins, defense protein or regulatory proteins such as antibodies, hormones and growth factors can be used. Proteineous or peptidic antigens can also be used.

Any suitable nucleic acids, including single-, double and triple-stranded nucleic acids, can be used. Examples of such nucleic acids include DNA, such as A-, B- or Z-form DNA, and RNA such as mRNA, tRNA and rRNA.

Any suitable nucleosides can be used. Examples of such nucleosides include adenosine, guanosine, cytidine, thymidine and uridine. Any suitable nucleotides can be used. Examples of such nucleotides include AMP, GMP, CMP, UMP, ADP, GDP, CDP, UDP, ATP, GTP, CTP, UTP, dAMP, dGMP, dCMP, dTMP, dADP, dGDP, dCDP, dTDP, dATP, dGTP, dCTP and dTTP.

Any suitable vitamins can be used. For example, water-soluble vitamins such as thiamine, riboflavin, nicotinic acid, pantothenic acid, pyridoxine, biotin, folate, vitamin $B_{12}$ and ascorbic acid can be used. Similarly, fat-soluble vitamins such as vitamin A, vitamin D, vitamin E, and vitamin K can be used.

Any suitable monosaccharides, whether D- or L-monosaccharides and whether aldoses or ketoses, can be used. Examples of monosaccharides include triose such as glyceraldehyde, tetroses such as erythrose and threose, pentoses such as ribose, arabinose, xylose, lyxose and ribulose, hexoses such as allose, altrose, glucose, m annose, gulose, idose, galactose, talose and fructose and heptose such as sedoheptulose.

Any suitable lipids can be used. Examples of lipids include triacylglycerols such as tristearin, tripalmitin and triolein, waxes, phosphoglycerides such as phosphatidylethanolamine, phosphatidylcholine, phosphatidylserine, phosphatidylinositol and cardiolipin, sphingolipids such as sphingomyelin, cerebrosides and gangliosides, sterols such as cholesterol and stigmasterol and sterol fatty acid esters. The fatty acids can be saturated fatty acids such as lauric acid, myristic acid, palmitic acid, stearic acid, arachidic acid and lignoceric acid, or can be unsaturated fatty acids such as palmitoleic acid, oleic acid, linoleic acid, linolenic acid and arachidonic acid.

The inner core of the present nanostructure can comprise any suitable material. For example, the material can comprise a polymer. In some embodiments, the polymer can be a hydrophobic polymer that coils when switched from an organic solvent to an aqueous phase, e.g., water. In some embodiments, the inner core of the nanostructure can comprise a biocompatible or a synthetic material, such as poly (lactic-co-glycolic acid) (PLGA), polylactic acid (PLA), poly (1-lactic acid) (PLLA), polyglycolic acid (PGA), polycaprolactone (PCL), polylysine, polyglutamic acid, poly (ethylene-co-vinyl acetate) (EVOH), poly(vinyl acetate) (PVA), polyethylene glycol (PEG), poly(glycerol sebacate) (PGS), polydioxanone (PDO), polyphosphazenes, polyurethane (PU) and modifications, analogs, and derivatives, thereof. In one preferred embodiment, the polymer is poly (lactic-c-glycolic acid) (PLGA). In some embodiments, the inner core of the nanostructure can comprise stainless steel, titan, nitinol, silver, gold, and mixtures or complexes thereof.

The present nanostructure can comprise any suitable membrane derived from a cell, a virus, and/or a cellular source. For example, the present nanostructure can comprise a plasma membrane or an intracellular membrane derived from a cell or a virus. In some embodiments, the membrane comprises a plasma membrane derived from blood cells (e.g. red blood cells), bone cells, neurons, immune cells, skin cells, muscle cells, cardiac cells, epithelial cells, cartilage cells, adispose cells, secretory cells (e.g. a beta cell), reproductive cells, and the like. In some embodiments, the present nanostructure can comprise any suitable naturally occurring membrane derived from a cell or a virus. In some embodiments, the cellular membrane comprises a naturally occurring plasma membrane derived from a beta cell, e.g., a naturally occurring plasma membrane derived from a human beta cell.

The membrane of the present nanostructure can be derived from any suitable unicellular organism or multicellular organism. In some embodiments, the membrane of the present nanostructure can be derived from a multicellular organism, e.g., an animal, a plant or a filamentous fungus. The animal can be an invertebrate or a vertebrate. The invertebrate can be an insect, a mollusc, a crustacean, a coral, an arachnid, a velvet worm, or a horseshoe crab. The vertebrate can be a fish, an amphibian, a reptile, a bird or a mammal. The mammal can be a non-human mammal. The non-human mammal can be a rodentia, e.g., a mice, a rat, a porcupine, a beaver, or a capybara, a chiroptera, e.g., a bat, a soricomorpha, e.g., a shrew, a mole or a solenodon, a primate, e.g., a prosimian such as a lemur of Madagascar, a lorisoid or a tarsier, or a simian such as a monkey, an ape or a hominin, a cetartiodactyla, e.g., a whale or an even-toed hoofed mammal, or a carnivora, e.g., a cat, a dog, a weasel, a bear, or a seal. The mammal can also be a human.

The membrane of the present nanostructure can be derived from any suitable type of cell. In some embodiments, the membrane of the present nanostructure can be derived from an animal cell. For example, the membrane can be derived from a cell of a connective tissue, e.g., a blood, a bone, a tendon, a ligament, an adipose or an areolar tissue, a muscle tissue, e.g., a smooth muscle, a skeletal muscle or a cardiac muscle (heart muscle), a nervous tissue, e.g., a tissue of central nervous system (CNS), such as brain and spinal cord, or peripheral nervous system (PNS), such as a cranial nerve and a spinal nerve, or an epithelial tissue, e.g., simple squamous epithelium, stratified squamous epithelium, simple cuboidal epithelium, transitional epithelium, pseudostratified columnar epithelium (AKA ciliated columnar epithelium), columnar epithelium, glandular epithelium, or ciliated columnar epithelium. In another example, the membrane can be derived from a cell of an organ system. Exemplar organ systems include a cardiovascular system, a digestive system, an endocrine system, an excretory system, a lymphatic system, an integumentary system, a muscular system, a nervous system, a reproductive system, a respiratory system and a skeletal system. In one specific embodiment, the membrane is derived from a blood cell. In another specific embodiment, the membrane comprises a plasma membrane derived from a red blood cell. In still another specific embodiment, the membrane is derived from a tumor cell, a cancer cell, an immune cell, a stem cell, an endothelial cell, a β cell, an exosome, a secretory vesicle or a synaptic vesicle.

In some embodiments, the membrane of the present nanostructure can be derived from a plant cell. Exemplar plants include a flowering plant, a conifer, a gymnosperm, a fern, a lycopodiopsida, a hornwort, a marchantiophyta, a moss and a green alga.

In some embodiments, the membrane of the present nanostructure can be derived from a filamentous fungus (mold). Exemplar filamentous fungi (mold) include an *Acremonium*, an *Alternaria*, an *Aspergillus*, a *Cladosporium*, a *Fusarium*, a *Mucor*, a *Penicillium*, a *Rhizopus*, a *Stachybotrys*, a *Trichoderma*, and a *Trichophyton*.

The membrane of the present nanostructure can be derived from any suitable unicellular organism. In some embodiments, the membrane of the present nanostructure can be derived from any suitable prokaryote. The prokaryote can be a bacterium or an archaeon. The membrane of the present nanostructure can be derived from any suitable bacterium. For example, the membrane of the present nanostructure can be derived from a pathogenic bacterium. The pathogenic bacterium can be a pathogenic bacterium that causes tuberculosis, e.g., *Mycobacterium tuberculosis*, pneumonia, e.g., a *streptococcus* or a *pseudomonas*, a foodborne illness, e.g., a *shigella*, a *campylobacter*, or a *salmonella*, tetanus, e.g., *Clostridium tetani*, typhoid fever, e.g., *Salmonella enterica* subsp. *enterica*, diphtheria, e.g., *Corynebacterium diphtherias*, syphilis, e.g., *Treponema pallidum*, or leprosy, e.g., *Mycobacterium leprae* or *Mycobacterium lepromatosis*.

In some embodiments, the membrane of the present nanostructure can be derived from any suitable eukaryote. For example, the membrane of the present nanostructure can be derived from a protozoa, e.g., an *euglenozoa*, an *amoebozoa*, a *choanozoa*, a *loukozoa*, a *percolozoa*, a *microsporidia* or a *sulcozoa*, an unicellular algae, e.g., an *euglenid*, a *chlorophyta*, a *diatom* or a *dinoflagellate*, or a unicellular fungi, e.g., a yeast such as *Saccharomyces cerevisiae* or *Candida*.

In some embodiments, the membrane of the present nanostructure can be derived from any suitable virus. For example, the membrane of the present nanostructure can be derived from a class I (dsDNA) virus, e.g., an adenoviruse, a herpesviruse, or a poxviruse, a class II (ssDNA) virus, e.g., a parvoviruse, a class III (dsRNA) virus, e.g., a reoviruse, a class IV ((+)ssRNA) virus, e.g., a picornaviruse or a togaviruse, a class V ((−)ssRNA) virus, e.g., an orthomyxoviruse or a rhabdoviruse, a class VI (ssRNA-RT) virus, e.g., a retroviruses, or a class VII (dsDNA-RT) virus, e.g., a hepadnaviruse.

The present nanostructure can further comprise a releasable cargo. The nanostructure can comprise a releasable cargo at any suitable location. For example, the releasable cargo can be located within or on the inner core, between the inner core and the outer surface, or within or on the outer surface. The release of the releasable cargo can be triggered by any suitable mechanisms. For example, the release of the releasable cargo can be triggered by a contact between the nanostructure and the subject or by a change of a physical parameter surrounding the nanostructure. The nanostructure can comprise any suitable types of releasable cargo. For example, the releasable cargo can be a therapeutic agent, a prophylactic agent, a diagnostic agent, a prognostic agent, a marker agent, a sensing agent, or a combination thereof. The therapeutic agent can be a cytotoxic drug capable of cell killing. Any suitable cytotoxic drugs can be used. For example, cytotoxic drugs can be an anthracycline, e.g., doxorubicin or daunorubicin, a taxane, e.g., docetaxel or paclitaxel, or an immunosuppressive agent, e.g., methotrexate or cyclosporin A. In another example, the releasable cargo can be a metallic particle, a polymeric particle, a dendrimer particle, or an inorganic particle or the releasable cargo can be in the form of a metallic particle, a polymeric particle, a dendrimer particle, or an inorganic particle.

In some embodiments, the present nanostructure substantially lacks constituents of the cell or virus from which the cellular or viral membrane is derived. In some embodiments, the present nanostructure substantially lacks cytoplasm, nucleus, nucleic acids, and/or cellular organelles of the cell or virus from which the cellular or viral membrane is derived. For example, the nanostructure can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the cell or virus, e.g., red blood cell, from which the cellular or viral membrane is derived. In some embodiments, the nanostructure comprises a plasma membrane derived from a red blood cell and the nanostructure substantially lacks hemoglobin. For example, the nanostructure can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the hemoglobin. In some embodiments, the membrane comprises a plasma membrane derived from a β cell and the nanostructure substantially lacks constituents of the β cell. For example, the nanostructure can lack about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the constituents of the β cell.

In some embodiments, the present nanostructure substantially maintains natural structural integrity or activity of the cellular or viral membrane or the constituents of the cellular or viral membrane. For example, the nanostructure can retain about 10%, 20%, 30%, 40%, 50%, 55%, 60%, 65%, 70%, 75%, 80%, 85%, 90%, 91%, 92%, 93%, 94%, 95%, 96%, 97%, 98%, 99%, or 100% of the natural structural integrity. In some embodiments, the nanostructure substantially maintains natural structural integrity of the cellular or viral membrane or the constituents of the cellular or viral membrane including primary, secondary, tertiary and/or quaternary structure of the cellular membrane, the membrane derived from a virus or the constituents of the cellular membrane or viral membrane. In some embodiments, the nanostructure substantially maintains activity of the cellular or viral membrane or the constituents of the cellular or viral membrane including binding activity, receptor activity, enzymatic activity, channeling activity, pumping activity, anchoring activity, supporting activity and/or signaling activity of the cellular membrane, the membrane derived from a virus or the constituents of the cellular membrane or viral membrane. In some embodiments, the outer surface of the nanostructure comprises a membrane that supports, facilitates and/or enables anchoring activity, attaching activity, supporting activity, interacting activity and/or signaling activity between the nanostructure and another cell.

In some embodiments, the present nanostructure is biocompatible or biodegradable. For example, the inner core of the nanostructure can comprise PLGA and the outer surface of the nanostructure can comprise a plasma membrane derived from a cell, e.g., a red blood cell, a tumor cell, a cancer cell, an immune cell, a stem cell, an endothelial cell, a β cell, and the like.

In some embodiments, the inner core comprises of the nanostructure comprises PCL and the outer surface comprises a plasma membrane derived from a β cell.

In some embodiments, the present nanostructure substantially lacks immunogenicity to a subject, a mammal, a non-human mammal or a human, to which the nanostructure may be configured to administer. For example, the membrane can be derived from a cell, e.g., a red blood cell or a beta cell, from the same species of the subject. In another example, the subject is a human and the membrane is derived from a human cell, e.g., a human red blood cell or a beta cell. In some embodiments, the membrane can be derived from a cell, e.g., a red blood cell or a beta cell, of the subject to be treated. For example, the membrane can be derived from a red blood cell or a beta cell of the human to be treated.

The outer surface of the present nanostructure can comprise a hybrid membrane comprising a membrane derived from a cell or virus and a synthetic membrane. In some embodiments, the outer surface of the present nanostructure can comprise a hybrid membrane comprising at least about 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w), 96% (w/w), 97% (w/w), 98% (w/w), 99% (w/w) of a cellular or viral membrane. In other embodiments, the outer surface of the present nanostructure can comprise a hybrid membrane comprising at least about 1% (w/w), 2% (w/w), 3% (w/w), 4% (w/w), 5% (w/w), 6% (w/w), 7% (w/w), 8% (w/w), 9% (w/w), 10% (w/w), 20% (w/w), 30% (w/w), 40% (w/w), 50% (w/w), 60% (w/w), 70% (w/w), 80% (w/w), 90% (w/w), 91% (w/w), 92% (w/w), 93% (w/w), 94% (w/w), 95% (w/w) of a synthetic membrane. For example, the outer surface of the present nanostructure can comprise a hybrid membrane comprising about 5-10% (w/w) of a cellular or viral membrane and about 95-99% (w/w) of a synthetic membrane, about 11-25% (w/w) of a cellular or viral membrane and about 75-89% (w/w) of a synthetic membrane, about 50% (w/w) of a cellular or viral membrane and about 50% (w/w) of a synthetic membrane, about 51-75% (w/w) of a cellular or viral membrane and about 49-25% (w/w) of a synthetic membrane, or about 90-99% (w/w) of a cellular or viral membrane and about 1-10% (w/w) of a synthetic membrane.

The naturally occurring cellular or viral membrane and/or the synthetic membrane in the outer surface of the present nanostructure can comprise a modification. The modification can be a physical modification, a chemical modification or a biological modification, e.g., a modification via genetic engineering. The naturally occurring cellular or viral membrane and/or the synthetic membrane can be modified to contain a small molecule or macromolecule, e.g., an amino acid, a peptide, a protein, a nucleoside, a nucleotide, an oligonucleotide, a nucleic acid, e.g., DNA or RNA, a vitamin, a monosaccharide, an oligosaccharide, a carbohydrate, a lipid, or an aggregate or a complex thereof. The naturally occurring cellular or viral membrane and/or the synthetic membrane can also be modified to contain an antigen, an epitope, a specific binder, e.g., a receptor, an antibody, a probe or a primer. The naturally occurring cellular or viral membrane and/or the synthetic membrane can further be modified to contain a moiety that confers a structure and/or an activity. Exemplary structures of a cellular or viral membrane include primary, secondary, tertiary and/or quaternary structures of the cellular or viral membrane. Exemplary activities of a cellular or viral membrane include binding activity, receptor activity, enzymatic activity, channeling activity, pumping activity, anchoring activity, supporting activity and/or signaling activity of the cellular or viral membrane. The modification can be used to alter, e.g., to enhance or weaken, the existing structures and/or activities of the cellular, viral or synthetic membrane. The modification can be used to add structures and/or activities to the cellular, viral or synthetic membrane.

The present nanostructure can have any suitable size. For example, the first dimension can have a first dimensional parameter, e.g., a length, width or diameter, from about 1 nm to about 10 µm. In certain embodiments, the first dimensional parameter e.g., a length, width or diameter, of the nanostructure is about 1 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, and 10 µm, or any sub-range within about 1 nm to about 10 µm, e.g., any range between any two of the above sizes.

The second dimension can have a second dimensional parameter, e.g., a length, width or diameter, of at least about 11 µm. For example, the second dimensional parameter, e.g., a length, width or diameter, can be at least about 11 µm, 12 µm, 13 µm, 14 µm, 15 µm, 16 µm, 17 µm, 18 µm, 19 µm, 20 µm, 30 µm, 40 µm, 50 µm, 60 µm, 70 µm, 80 µm, 90 µm, 100 µm, 200 µm, 300 µm, 400 µm, 500 µm, 600 µm, 700 µm, 800 µm, 900 µm, 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 mm, 400 mm, 500 mm, 600 mm, 700 mm, 800 mm, 900 mm, 1 m, 2 m, 3 m, 4 m, 5 m, 6 m, 7 m, 8 m, 9 m, 10 m, 20 m, 30 m, 40 m, 50 m, 60 m, 70 m, 80 m, 90 m, 100 m or longer, or any sub-range within about 11 µm to about 100 m, e.g., any range between any two of the above sizes.

The present nanostructure can have any suitable ratio between the second dimensional parameter, e.g., a length, width or diameter, and the first dimensional parameter, e.g., a length, width or diameter. For example, the ratio between the second dimensional parameter, e.g., a length, width or diameter, and the first dimensional parameter, e.g., a length, width or diameter, can be at least about 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900,000, 1,000,000, 2,000,000, 3,000,000, 4,000,000, 5,000,000, 6,000,000, 7,000,000, 8,000,000, 9,000,000, 10,000,000, or larger, or any sub-range within about 2 to about 10,000,000, e.g., any range between any two of the above ratios.

In some embodiments, the second dimension can have a second dimensional parameter, e.g., a length, width or diameter, of at least about 11 µm and the ratio between the second dimensional parameter, e.g., a length, width or diameter, and the first dimensional parameter, e.g., a length, width or diameter, can be at least about 2, 3, 4, 5, 6, 7, 8, 9, 10.

In some embodiments, the second dimensional parameter, e.g., a length, width or diameter, can be at least about 1 mm. In other embodiments, the ratio between the second dimensional parameter, e.g., a length, width or diameter, and the first dimensional parameter, e.g., a length, width or diameter, can be at least about 1,000. In still other embodiments, the second dimensional parameter, e.g., a length, width or diameter, can be at least about 1 mm and the ratio between the second dimensional parameter, e.g., a length, width or diameter, and the first dimensional parameter, e.g., a length, width or diameter, can be at least about 1,000.

In some embodiments, the present nanostructure can be configured as 1 D nanostructure, e.g., a nanofiber, nanotube or nanowire. The 1 D nanostructure can have any suitable second dimensional parameter, e.g., a length, width or diameter. For example, the second dimensional parameter, e.g., a length, width or diameter, in the 1 D nanostructure can be at least about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 mm, 400 mm, 500 mm, 600 mm, 700 mm, 800 mm, 900 mm, 1 m, 2 m, 3 m, 4 m, 5 m, 6 m, 7 m, 8 m, 9 m, 10 m, 20 m, 30 m, 40 m, 50 m, 60 m, 70 m, 80 m, 90 m, 100 m or longer, or any sub-range within about 1 mm to about 100 m, e.g., any range between any two of the above sizes.

The present nanostructure can have any suitable shape. For example, the first dimension of the present nanostructure can have a shape that comprises straight line segments, a shape that comprises a polygon with specific numbers of sides, a shape that comprises a circular arc, or a shape that does not comprise a circular arc. The shape that comprises straight line segments can be a balbis, a concave polygon, a constructible polygon, a convex polygon, a cyclic polygon, an equiangular polygon, an equilateral polygon, a Penrose tile, a polyform, a regular polygon, a simple polygon or a tangential polygon. The shape that comprises a polygon with specific numbers of sides can be a monogon, a digon, a triangle, a quadrilateral, a pentagon, a hexagon, a heptagon, an octagon, a nonagon, a decagon, a hendecagon, a dodecagon, a hexadecagon, an icosagon or a star polygon. The shape that comprises a circular arc can be an annulus, an arbelos, a circle, e.g., Archimedes' twin circles, a Bankoff circle, a circumcircle, a disc, an excircle, an incircle, or a nine-point circle, a circular sector, a circular segment, a crescent, an Indalo, a lens, a lune, a Reuleaux polygon, e.g., a Reuleaux triangle, a salinon, a semicircle, a tomahawk or a triquetra. The shape that does not comprise a circular arc can be an Archimedean spiral, an astroid, a cardioid, a deltoid, an ellipse, a heart (geometry), a heartagon, a lemniscate, an oval, e.g., a Cartesian oval, a Cassini oval or an Oval of Booth, an ovoid (shape), a superellipse, a taijitu or tomoe. In some embodiments, the first dimension of the present nanostructure can have a shape comprising a sphere, a square, a rectangle, a triangle, a circular disc and other regular or irregular shape.

The present nanostructure can further comprise a third dimension with a third dimensional parameter, e.g., a length, width or diameter, from about 1 nm to about 10 µm. For example, the third dimensional parameter, e.g., a length, width or diameter, can be at least about 1 nm, 10 nm, 20 nm, 30 nm, 40 nm, 50 nm, 60 nm, 70 nm, 80 nm, 90 nm, 100 nm, 110 nm, 120 nm, 130 nm, 140 nm, 150 nm, 200 nm, 300 nm, 400 nm, 500 nm, 600 nm, 700 nm, 800 nm, 900 nm, 1 µm, 2 µm, 3 µm, 4 µm, 5 µm, 6 µm, 7 µm, 8 µm, 9 µm, or 10 µm, or any sub-range within about 1 nm to about 10 µm, e.g., any range between any two of the above sizes.

The present nanostructure can have any suitable ratio between the third dimensional parameter, e.g., a length, width or diameter, and the first dimensional parameter, e.g., a length, width or diameter. For example, the ratio between the third dimensional parameter, e.g., a length, width or diameter, and the first dimensional parameter, e.g., a length, width or diameter, can be at least about 1, 2, 3, 4, 5, 6, 7, 8, 9, 10, 20, 30, 40, 50, 60, 70, 80, 90, 100, 200, 300, 400, 500, 600, 700, 800, 900, or 1,000, or any sub-range within about 1 to about 1,000, e.g., any range between any two of the above ratios.

In some embodiments, the third dimension can have a third dimensional parameter, e.g., a length, width or diameter, of at least about 1 nm and the ratio between the third dimensional parameter, e.g., a length, width or diameter, and the first dimensional parameter, e.g., a length, width or diameter, can be at least about 1.

In some embodiments, the third dimensional parameter, e.g., a length, width or diameter, can be at least about 1 μm. In other embodiments, the ratio between the third dimensional parameter, e.g., a length, width or diameter, and the first dimensional parameter, e.g., a length, width or diameter, can be at least about 1,000. In still other embodiments, the third dimensional parameter, e.g., a length, width or diameter, can be at least about 1 μm and the ratio between the third dimensional parameter, e.g., a length, width or diameter, and the first dimensional parameter, e.g., a length, width or diameter, can be at least about 1,000.

In some embodiments, the present nanostructure can be configured as 2 D nanostructure, e.g., a nanosheet. The 2 D nanostructure can have any suitable second and third dimensional parameters, e.g., a length, width or diameter. For example, the second dimensional parameter, e.g., a length, width or diameter, in the 2 D nanostructure can be at least about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 mm, 400 mm, 500 mm, 600 mm, 700 mm, 800 mm, 900 mm, 1 m, 2 m, 3 m, 4 m, 5 m, 6 m, 7 m, 8 m, 9 m, 10 m, 20 m, 30 m, 40 m, 50 m, 60 m, 70 m, 80 m, 90 m, 100 m or longer, or any sub-range within about 1 mm to about 100 m, e.g., any range between any two of the above sizes. In another example, the third dimensional parameter, e.g., a length, width or diameter, in the 2 D nanostructure can be at least about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 mm, 400 mm, 500 mm, 600 mm, 700 mm, 800 mm, 900 mm, 1 m, 2 m, 3 m, 4 m, 5 m, 6 m, 7 m, 8 m, 9 m, 10 m, 20 m, 30 m, 40 m, 50 m, 60 m, 70 m, 80 m, 90 m, 100 m or longer, or any sub-range within about 1 mm to about 100 m, e.g., any range between any two of the above sizes. In still another example, both of the second and third dimensional parameters, e.g., a length, width or diameter, in the 2 D nanostructure can be at least about 1 mm, 2 mm, 3 mm, 4 mm, 5 mm, 6 mm, 7 mm, 8 mm, 9 mm, 10 mm, 20 mm, 30 mm, 40 mm, 50 mm, 60 mm, 70 mm, 80 mm, 90 mm, 100 mm, 200 mm, 300 mm, 400 mm, 500 mm, 600 mm, 700 mm, 800 mm, 900 mm, 1 m, 2 m, 3 m, 4 m, 5 m, 6 m, 7 m, 8 m, 9 m, 10 m, 20 m, 30 m, 40 m, 50 m, 60 m, 70 m, 80 m, 90 m, 100 m or longer, or any sub-range within about 1 mm to about 100 m, e.g., any range between any two of the above sizes.

In some embodiments, the present 2 D nanostructure, e.g., a nanosheet, can have a length, width and thickness, and the thickness dimension has a dimensional parameter ranging from about 1 nm to about 10 μm. A ratio between the length and thickness can be at least about 10. A ratio between the width and thickness can be at least about 10. A ratio between the length and thickness and a ratio between the width and thickness can both be at least about 10.

The inner core of the present 2 D nanostructure can comprise any suitable material. For example, the inner core of the present 2 D nanostructure can comprise carbon atoms, e.g., graphene, or metal atoms, e.g., palladium, rhodium, or gold atoms.

In some embodiments, the inner core of the present nanostructure, e.g., the present 1 or 2 D nanostructure, can have any suitable shape. For example, the inner core of the present nanostructure can have a shape, including but not limited to, sphere, square, rectangle, triangle, circular disc, cube-like shape, cube, rectangular parallelepiped (cuboid), cone, cylinder, prism, pyramid, right-angled circular cylinder, line, rod, sheet, plain, plate, and other regular or irregular shape.

In some embodiments, the inner core supports the outer surface in the present nanostructure.

The inner core of the present nanostructure can be prepared by any suitable technbique or process. In some embodiments, the inner core can be prepared by a top-down or a bottom-up process. In other embodiments, the inner core can be prepared by lithography, electrophoresis, suspension, electrochemical deposition, vapor deposition, vapor-liquid-solid method (VLS), ion track, melt processing, interfacial polymerization, electrospinning, antisolvent-induced polymer precipitation, electrostatic spinning, catalytic synthesis, solution phase synthesis or "island in the sea." See e.g., Xiangwu Zhang, Ph.D., Xiangwu (Jan. 1, 2014). Fundamentals of Fiber Science (1st ed.). Lancaster Pa.: DEStech Publications, Inc. p. 426. ISBN 978-1-60595-119-5.

The present nanostructure can be prepared by any suitable technique or process. In some embodiments, the present nanostructure can be prepared by combining the inner core and the outer surface to form the nanostructure. In other embodiments, the inner core and the outer surface can be combined in the presence of exogenous energy on the combination to form the nanostructure. Any suitable exogenous energy can be used. For example, the exogenous energy can be a mechanical energy, an acoustic energy, or a thermal energy.

In some aspects, the invention also provides a nanostructure network comprising multiple nanostructures described above as constituents of said nanostructure network.

The present nanostructure network can comprise any suitable number of the above nanostructures. For example, the present nanostructure network can comprise at least 2 of the above nanostructures, e.g., at least about 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800,000, 900, 000, 1,000,000, 2,000,000, 3,000,000, 4,000,000, 5,000,000, 6,000,000, 7,000,000, 8,000,000, 9,000,000, 10,000,000, or more of the above nanostructures, or any sub-range within about 10 to about 10,000,000, e.g., any range between any two of the above nanostructures.

In some aspects, the invention further provides a nanoscaffold comprising a single layer or multiple layers of the nanostructure networks described above as constituents of said nanoscaffold.

The present nanoscaffold can comprise any suitable layers of the above nanostructure networks. For example, the present nanostructure network can comprise at least 1 layer of the above nanostructures, e.g., at least about 1, 2, 3, 4, 5, 6, 7, 8, 9, 10, 20, 30, 40, 50, 60, 70, 80, 90, 100, 200, 300, 400, 500, 600, 700, 800, 900, 1,000, 2,000, 3,000, 4,000, 5,000, 6,000, 7,000, 8,000, 9,000, 10,000, 20,000, 30,000, 40,000, 50,000, 60,000, 70,000, 80,000, 90,000, 100,000, 200,000, 300,000, 400,000, 500,000, 600,000, 700,000, 800, 000, 900,000, 1,000,000, 2,000,000, 3,000,000, 4,000,000, 5,000,000, 6,000,000, 7,000,000, 8,000,000, 9,000,000, 10,000,000, or more layer(s) of the above nanostructure networks, or any sub-range within about 2 to about 10,000,000, e.g., any range between any two layers of the above nanostructure networks.

In some aspects, the invention further provides an article of manufacture comprising the nanostructure described above, the nanostructure network described above, or the nanoscaffold described above.

The present article of manufacture can be configured for any suitable use. For example, the present article of manufacture can be configured for in vivo or ex vivo use. In some embodiments, the present article of manufacture can be configured as an implantable material, composition or device. In other embodiments, the present article of manufacture can be configured for a health care or medical application, e.g., as artificial organ component, tissue engineering component, implant material, drug delivery vehicle, wound dressing material, medical textile material, anti-infection agent, contraception material, or wound healing material. In still other embodiments, the present article of manufacture can be configured for treating and/or preventing a disease or condition in a subject. In yet other embodiments, the present article of manufacture can be for sensing a parameter, a disease or a condition in a subject.

In other examples, the present article of manufacture can be configured for in vitro use. In some embodiments, the present article of manufacture can be configured as a part of a surface, a container, a device, a kit or a system. In other embodiments, the present article of manufacture can be configured for anchoring, attaching and/or growing a target cell, e.g., a functional target cell. In still other embodiments, the present article of manufacture can be configured as a part of a sensing device or system, e.g., a field-effect transistor (FET) sensing device. In still other embodiments, the present article of manufacture can be configured as a part of a protective material, e.g., a sound absorption material or protective clothing against a chemical and biological warfare agent. In yet other embodiments, the present article of manufacture can be configured as a part of a cosmetic. In yet other embodiments, the present article of manufacture can be configured to be used in the textile industry, e.g., as a part of an apparel, a shoe, a baby diaper, a napkin, etc. In yet other embodiments, the present article of manufacture can be configured as a part of a self-twisting or self-brading nanostructure, e.g., nanofibers.

In some aspects, the invention further provides a medicament delivery system or a medical device, which comprises an effective amount of the nanostructure described above, the nanostructure network described above, the nanoscaffold of described above, or the article of manufacture described above. The present medicament delivery system or medical device can further comprise another active ingredient, and/or a medically and/or pharmaceutically acceptable carrier or excipient.

In some aspects, the invention further provides a pharmaceutical composition, which pharmaceutical composition comprises an effective amount of the nanostructure described above, the nanostructure network described above, the nanoscaffold described above, or the article of manufacture described above and a pharmaceutically acceptable carrier or excipient. The present pharmaceutical can further comprise another active ingredient.

In some aspects, the invention further provides a method for treating and/or preventing a disease or condition in a subject, which method comprises administering, to a subject in need of such treatment and/or prevention, an effective amount of the nanostructure described above, the nanostructure network described above, the nanoscaffold described above, or the article of manufacture described above, or the pharmaceutical composition described above.

The present method can be used for treating and/or preventing any suitable disease or condition. For example, the present method can be used for treating and/or preventing an infectious disease, a parasitic disease, a neoplasm, a cancer, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity or mortality.

The present method can be used for treating and/or preventing a disease or condition in any suitable subject. For example, the present method can be used for treating and/or preventing a disease or condition in an invertebrate or a vertebrate. The invertebrate can be an insect, a mollusc, a crustacean, a coral, an arachnid, a velvet worm, or a horseshoe crab. The vertebrate can be a fish, an amphibian, a reptile, a bird or a mammal. The mammal can be a non-human mammal. The non-human mammal can be a rodentia, e.g., a mice, a rat, a porcupine, a beaver, or a capybara, a chiroptera, e.g., a bat, a soricomorpha, e.g., a shrew, a mole or a solenodon, a primate, e.g., a prosimian such as a lemur of Madagascar, a lorisoid or a tarsier, or a simian such as a monkey, an ape or a hominin, a cetartiodactyla, e.g., a whale or an even-toed hoofed mammal, or a carnivora, e.g., a cat, a dog, a weasel, a bear, or a seal. The mammal can also be a human.

In some embodiments, the membrane in the present nanostructure, nanostructure network, nanoscaffold, article of manufacture, or pharmaceutical composition can be derived from a cell of the same species of the subject or is derived from a cell of the subject. For example, the membrane in the present nanostructure, nanostructure network, nanoscaffold, article of manufacture, or pharmaceutical composition can be derived from a red blood cell of the same species of the subject and the red blood cell has the same blood type of the subject.

The present methods can further comprise administering another active ingredient to the subject and/or a pharmaceutically acceptable carrier or excipient to the subject, or the present nanostructure, nanostructure network, nanoscaffold, article of manufacture, or pharmaceutical composition is administered via a medicament delivery system.

The present nanostructure, nanostructure network, nanoscaffold, article of manufacture, or pharmaceutical composition can be administered via any suitable route. For example, the present nanostructure, nanostructure network, nanoscaffold, article of manufacture, or pharmaceutical composition can be administered via an oral, nasal, inhalational, parental, intravenous, intraperitoneal, subcutaneous, intramuscular, intradermal, topical, or rectal route. In another example, the present nanostructure, nanostructure network, nanoscaffold, article of manufacture, or pharmaceutical composition can be administered to a target dermal site or blood.

In some aspects, the invention further provides a use of an effective amount of the present nanostructure, nanostructure network, nanoscaffold, article of manufacture for the manufacture of a medicament for treating and/or preventing a disease or condition in a subject.

C. METHODS FOR ANCHORING, ATTACHING AND/OR GROWING A TARGET CELL

In another aspect, the present invention provides for a method for anchoring, attaching and/or growing a target cell, which method comprises contacting a target cell with a nanostructure under conditions that allow said target cell to anchor on or attach to said nanostructure and/or grow, wherein said nanostructure comprises an inner core comprising a non-cellular material and an outer surface comprising a membrane derived from a source cell or virus, and wherein said membrane derived from said source cell or virus allows said target cell to anchor on or attach to said nanostructure.

The target cell can be contacted with any suitable nanostructure. For example, the target cell can be contacted with the nanostructure, the nanostructure network, the nanoscaffold, or the article of manufacture described above.

The present methods can be used for anchoring, attaching and/or growing any suitable target cell. For example, the present methods can be used for anchoring, attaching and/or growing a target cell of a unicellular organism or a multicellular organism. In some embodiments, the present methods can be used for anchoring, attaching and/or growing a target cell of a multicellular organism, e.g., an animal, a plant or a filamentous fungus. The animal can be an invertebrate or a vertebrate. The invertebrate can be an insect, a mollusc, a crustacean, a coral, an arachnid, a velvet worm, or a horseshoe crab. The vertebrate can be a fish, an amphibian, a reptile, a bird or a mammal. The mammal can be a non-human mammal. The non-human mammal can be a rodentia, e.g., a mice, a rat, a porcupine, a beaver, or a capybara, a chiroptera, e.g., a bat, a soricomorpha, e.g., a shrew, a mole or a solenodon, a primate, e.g., a prosimian such as a lemur of Madagascar, a lorisoid or a tarsier, or a simian such as a monkey, an ape or a hominin, a cetartiodactyla, e.g., a whale or an even-toed hoofed mammal, or a carnivora, e.g., a cat, a dog, a weasel, a bear, or a seal. The mammal can also be a human.

The present methods can be used for anchoring, attaching and/or growing a cell of any suitable tissue. For example, the present methods can be used for anchoring, attaching and/or growing a cell of a connective tissue, e.g., a blood, a bone, a tendon, a ligament, an adipose or an areolar tissue, a muscle tissue, e.g., a smooth muscle, a skeletal muscle or a cardiac muscle (heart muscle), a nervous tissue, e.g., a tissue of central nervous system (CNS), such as brain and spinal cord, or peripheral nervous system (PNS), such as a cranial nerve and a spinal nerve, or an epithelial tissue, e.g., simple squamous epithelium, stratified squamous epithelium, simple cuboidal epithelium, transitional epithelium, pseudostratified columnar epithelium (AKA ciliated columnar epithelium), columnar epithelium, glandular epithelium, or ciliated columnar epithelium.

The present methods can be used for anchoring, attaching and/or growing a cell of any suitable organ system. For example, the present methods can be used for anchoring, attaching and/or growing a cell of a cell of a cardiovascular system, a digestive system, an endocrine system, an excretory system, a lymphatic system, an integumentary system, a muscular system, a nervous system, a reproductive system, a respiratory system or a skeletal system.

In some embodiments, the membrane of the nanostructure, the nanostructure network, the nanoscaffold, or the article of manufacture used in the present methods can be derived from a blood cell, e.g., a plasma membrane derived from a red blood cell. In other embodiments, the membrane of the nanostructure, the nanostructure network, the nanoscaffold, or the article of manufacture used in the present methods can be derived from a tumor cell, a cancer cell, an immune cell, a stem cell, an endothelial cell, a β cell, an exosoine, a secretory vesicle or a synaptic vesicle.

The present methods can be used for anchoring, attaching and/or growing a cell of any suitable plant cell. For example, the present methods can be used for anchoring, attaching and/or growing a cell of a flowering plant, a conifer, a gymnosperm, a fern, a lycopodiopsida, a hornwort, a marchantiophyta, a moss or a green alga.

The present methods can be used for anchoring, attaching and/or growing a cell of any suitable filamentous fungus (mold) cell. For example, the present methods can be used for anchoring, attaching and/or growing a cell of an *Acremonium*, an *Alternaria*, an *Aspergillus*, a *Cladosporium*, a *Fusarium*, a *Mucor*, a *Penicillium*, a *Rhizopus*, a *Stachybotrys*, a *Trichoderma*, and a *Trichophyton*.

The present methods can be used for anchoring, attaching and/or growing a target cell of unicellular organism. For example, the present methods can be used for anchoring, attaching and/or growing a cell of prokaryote such as a bacterium or an archaeon. The present methods can be used for anchoring, attaching and/or growing any suitable bacterial cell. The bacterial cell can be a cell of a pathogenic bacterium. Exemplary pathogenic bacteria include a pathogenic bacterium that causes tuberculosis, e.g., *Mycobacterium tuberculosis*, pneumonia, e.g., a *streptococcus* or a *pseudomonas*, a foodborne illness, e.g., a *shigella*, a *campylobacter*, or a *salmonella*, tetanus, e.g., *Clostridium tetani*, typhoid fever, e.g., *Salmonella enterica* subsp. *enterica*, diphtheria, e.g., *Corynebacterium diphtherias*, syphilis, e.g., *Treponema pallidum*, or leprosy, e.g., *Mycobacterium leprae* or *Mycobacterium lepromatosis*.

The present methods can be used for anchoring, attaching and/or growing a eukaryotic target cell. For example, The present methods can be used for anchoring, attaching and/or growing a cell of a protozoa, e.g., an *euglenozoa*, an *amoebozoa*, a *choanozoa*, a *loukozoa*, a *percolozoa*, a *microsporidia* or a *sulcozoa*, an unicellular algae, e.g., an *euglenid*, a *chlorophyta*, a *diatom* or a *dinoflagellate*, or a unicellular fungi, e.g., a yeast such as *Saccharomyces cerevisiae* or *Candida*.

The source cell and the target cell can belong to the same species, e.g., human. In some embodiments, the source cell and the target cell can belong to the same species of a multicellular organism, and the source cell and the target cell can belong to the same type of tissue, organ or system of the multicellular organism, e.g., blood. For example, the source cell and the target cell can be the same type of cell, e.g., red blood cell. The source cell and the target cell can have the same blood type. In some embodiments, the source cell and the target cell can be derived from the same subject, e.g., a mammal or a human.

The present methods can be used for any suitable purposes. For example, the present methods can be used to anchor the target cell on the nanostructure or attach the target cell to the nanostructure. In another example, the present methods can be used to grow the target cell. In another example, the present methods can be used to anchor or attach and/or grow a functional target cell. The functional target cell can have any suitable activity of the target cell. The activity of the target cell can be a physical, chemical or biological activity of the target cell.

In some embodiments, the biological activity of the target cell can relate to cellular metabolism, cellular reproduction, replication, transcription, translation, cell transport, cell death, e.g., programmed cell death, cellular senescence, cell signaling, cell adhesion, motility and cell migration, cytoplasmic streaming, and/or DNA repair. The cellular metabolism can be cellular respiration, e.g., glycolysis, citric acid cycle or electron transport chain, photosynthesis, e.g., light-dependent reactions, the Calvin cycle, or electron transport chain, metabolic pathway, ethanol fermentation, lactic acid fermentation, or chemosynthesis. The cellular reproduction can be cell cycle, meiosis or binary fission. The cell transport can be osmosis, passive transport, active transport, bulk transport, e.g., endocytosis or exocytosis, phagocytosis or tonicity. The activity of the target cell can be a binding activity, a receptor activity, an enzymatic activity, a channeling activity, a pumping activity, an anchoring activity, a supporting activity, a signaling activity, a producing activity and/or differentiating activity of the target cell.

The present methods can further comprise isolating, concentrating, enriching, purifying and/or collecting the target cell, or constituent(s) or culture medium of the target cell.

In some embodiments, the target cell secrets or transports a target substance to the outside of the target cell. The present methods can further comprise isolating, concentrating, enriching, purifying and/or collecting the target substance or culture medium of the target cell.

In some aspects, the invention further provides for a target cell, constituent(s) of the target cell, a target substance or culture medium of the target cell prepared by the above methods.

The present target cell, constituent(s) of the target cell, a target substance or culture medium of the target cell can be configured for any suitable uses.

The present target cell, constituent(s) of the target cell, a target substance or culture medium of the target cell can be configured for in vivo or ex vivo use. In some embodiments, the present target cell, constituent(s) of the target cell, a target substance or culture medium of the target cell can be configured as an implantable material, composition or device. In some embodiments, the present target cell, constituent(s) of the target cell, a target substance or culture medium of the target cell can be configured for a health care or medical application, e.g., as artificial organ component, tissue engineering component, implant material, drug delivery vehicle, wound dressing material, medical textile material, anti-infection agent, contraception material, or wound healing material. In some embodiments, the present target cell, constituent(s) of the target cell, a target substance or culture medium of the target cell can be configured for treating and/or preventing a disease or condition in a subject. In some embodiments, the present target cell, constituent(s) of the target cell, a target substance or culture medium of the target cell can be configured for sensing a parameter, a disease or a condition in a subject.

The present target cell, constituent(s) of the target cell, a target substance or culture medium of the target cell can be configured for in vitro use. In some embodiments, the present target cell, constituent(s) of the target cell, a target substance or culture medium of the target cell can be configured as a part of a surface, a container, a device, a kit or a system. In some embodiments, the present target cell, constituent(s) of the target cell, a target substance or culture medium of the target cell can be configured as a part of a sensing device or system, e.g., a field-effect transistor (FET) sensing device. In some embodiments, the present target cell, constituent(s) of the target cell, a target substance or culture medium of the target cell can be configured as a part of a protective material, e.g., a sound absorption material or protective clothing against a chemical and biological warfare agent, or as a part of a cosmetic. In some embodiments, the present target cell, constituent(s) of the target cell, a target substance or culture medium of the target cell can be configured to be used in the textile industry, e.g., as a part of an apparel, a shoe, a baby diaper, a napkin, etc. In some embodiments, the present target cell, constituent(s) of the target cell, a target substance or culture medium of the target cell can be configured as a part of a self-twisting or self-brading nanostructure, e.g., nanofibers.

In some embodiments, the present target cell, constituent(s) of the target cell, a target substance or culture medium of the target cell can be configured for research, development, drug screening, pre-clinical study, clinical study, diagnosis, prognosis, prevention of a disease or a condition, treatment of a disease or a condition, or prevention or treatment monitoring.

In some aspects, the invention further provides for a medicament delivery system or a medical device, which comprises an effective amount of the present target cell, constituent(s) of the target cell, a target substance or culture medium of the target cell. The medicament delivery system or medical device can further comprise another active ingredient, and/or a medically and/or pharmaceutically acceptable carrier or excipient.

In some aspects, the invention further provides for a pharmaceutical composition, which pharmaceutical composition comprises an effective amount of the present target cell, constituent(s) of the target cell, a target substance or culture medium of the target cell and a pharmaceutically acceptable carrier or excipient. The pharmaceutical composition can further comprise another active ingredient.

In some aspects, the invention further provides for a method for treating and/or preventing a disease or condition in a subject, which method comprises administering, to a subject in need of such treatment and/or prevention, an effective amount of the present target cell, constituent(s) of the target cell, a target substance or culture medium of the target cell.

The present method can be used for treating and/or preventing any suitable disease or condition. For example, the present method can be used for treating and/or preventing an infectious disease, a parasitic disease, a neoplasm, a cancer, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity or mortality.

The present methods can be used for treating and/or preventing a disease or condition in any suitable subject. For example, the present method can be used for treating and/or preventing a disease or condition in an invertebrate or a vertebrate. The invertebrate can be an insect, a mollusc, a crustacean, a coral, an arachnid, a velvet worm, or a horseshoe crab. The vertebrate can be a fish, an amphibian, a reptile, a bird or a mammal. The mammal can be a non-human mammal. The non-human mammal can be a rodentia, e.g., a mice, a rat, a porcupine, a beaver, or a capybara, a chiroptera, e.g., a bat, a soricomorpha, e.g., a shrew, a mole or a solenodon, a primate, e.g., a prosimian such as a lemur of Madagascar, a lorisoid or a tarsier, or a simian such as a monkey, an ape or a hominin, a cetartiodactyla, e.g., a whale or an even-toed hoofed mammal, or a carnivora, e.g., a cat, a dog, a weasel, a bear, or a seal. The mammal can also be a human.

The present methods can further comprise administering another active ingredient to the subject and/or a pharmaceutically acceptable carrier or excipient to the subject, or the present target cell, constituent(s) of the target cell, a target substance or culture medium of the target cell can be administered via a medicament delivery system.

The present target cell, constituent(s) of the target cell, a target substance or culture medium of the target cell can be administered via any suitable route. For example, the present target cell, constituent(s) of the target cell, a target substance or culture medium of the target cell can be administered via an oral, nasal, inhalational, parental, intravenous, intraperitoneal, subcutaneous, intramuscular, intradermal, topical, or rectal route. In another example, the present target cell, constituent(s) of the target cell, a target substance or culture medium of the target cell can be administered to a target dermal site or blood.

In some aspects, the invention further provides a use of an effective amount of the present target cell, constituent(s) of the target cell, a target substance or culture medium of the target cell for the manufacture of a medicament for treating and/or preventing a disease or condition in a subject.

D. PHARMACEUTICAL COMPOSITIONS AND ADMINISTRATION ROUTES

The pharmaceutical compositions comprising the present nanostructure, nanostructure network, nanoscaffold, article of manufacture, or the the present target cell, constituent(s) of the target cell, a target substance or culture medium of the target cell ("active substance"), alone or in combination with other active ingredient(s), described herein may further comprise one or more pharmaceutically-acceptable excipients. A pharmaceutically-acceptable excipient is a substance that is non-toxic and otherwise biologically suitable for administration to a subject. Such excipients facilitate administration of the nanostructure, alone or in combination with other active ingredient(s), described herein and are compatible with the active ingredient. Examples of pharmaceutically-acceptable excipients include stabilizers, lubricants, surfactants, diluents, anti-oxidants, binders, coloring agents, bulking agents, emulsifiers, or taste-modifying agents. In preferred embodiments, pharmaceutical compositions according to the various embodiments are sterile compositions. Pharmaceutical compositions may be prepared using compounding techniques known or that become available to those skilled in the art.

Sterile compositions are within the present disclosure, including compositions that are in accord with national and local regulations governing such compositions.

The pharmaceutical compositions and the active substance, alone or in combination with other active ingredient(s), described herein may be formulated as solutions, emulsions, suspensions, or dispersions in suitable pharmaceutical solvents or carriers, or as pills, tablets, lozenges, suppositories, sachets, dragees, granules, powders, powders for reconstitution, or capsules along with solid carriers according to conventional methods known in the art for preparation of various dosage forms. The active substance, alone or in combination with other active ingredient(s), described herein, and preferably in the form of a pharmaceutical composition, may be administered by a suitable route of delivery, such as oral, parenteral, rectal, nasal, topical, or ocular routes, or by inhalation. In some embodiments, the compositions are formulated for intravenous or oral administration.

For oral administration, the active substance, alone or in combination with another active ingredient, may be provided in a solid form, such as a tablet or capsule, or as a solution, emulsion, or suspension. To prepare the oral compositions, the active substance, alone or in combination with other active ingredient(s), may be formulated to yield a dosage of, e.g., from about 0.01 to about 50 mg/kg daily, or from about 0.05 to about 20 mg/kg daily, or from about 0.1 to about 10 mg/kg daily. Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinylpyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid, or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil, such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions, or syrups, or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The compositions may be formulated for rectal administration as a suppository. For parenteral use, including intravenous, intramuscular, intraperitoneal, intranasal, or subcutaneous routes, the nanostructure, alone or in combination with other active ingredient(s), may be provided in sterile aqueous solutions or suspensions, buffered to an appropriate pH and isotonicity or in parenterally acceptable oil. Suitable aqueous vehicles can include Ringer's solution and isotonic sodium chloride. Such forms may be presented in unit-dose form such as ampoules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For nasal, inhaled, or oral administration, the active substance, alone or in combination with other active ingredient(s), may be administered using, for example, a spray formulation also containing a suitable carrier.

For topical applications, the active substance, alone or in combination with other active ingredient(s), are preferably formulated as creams or ointments or a similar vehicle suitable for topical administration. For topical administration, the active substance, alone or in combination with other active ingredient(s), may be mixed with a pharmaceutical carrier at a concentration of about 0.1% to about 10% of drug to vehicle. Another mode of administering the active substance, alone or in combination with other active ingredient(s), may utilize a patch formulation to effect transdermal delivery.

In certain embodiments, the present disclosure provides pharmaceutical composition comprising the active substance, alone or in combination with other active ingredient(s), and methylcellulose. In certain embodiments, methylcellulose is in a suspension of about 0.1, 0.2, 0.3, 0.4, or 0.5 to about 1%. In certain embodiments, methylcellulose is in a suspension of about 0.1 to about 0.5, 0.6, 0.7, 0.8, 0.9, or 1%. In certain embodiments, methylcellulose is in a suspension of about 0.1 to about 1%. In certain embodiments, methylcellulose is in a suspension of about 0.1, 0.2, 0.3, 0.4, 0.5, 0.6, 0.7, 0.8, 0.8, or 1%. In certain embodiments, methylcellulose is in a suspension of about 0.5%.

As used herein, "preventative" treatment is meant to indicate a postponement of development of a disease, a symptom of a disease, or medical condition, suppressing symptoms that may appear, or reducing the risk of developing or recurrence of a disease or symptom. "Curative" treatment includes reducing the severity of or suppressing the worsening of an existing disease, symptom, or condition.

One of ordinary skill in the art may modify the formulations within the teachings of the specification to provide numerous formulations for a particular route of administration. In particular, the active substance, alone or in combination with other active ingredient(s), may be modified to render them more soluble in water or other vehicle. It is also well within the ordinary skill of the art to modify the route of administration and dosage regimen of a particular active substance, alone or in combination with other active ingredient(s), in order to manage the pharmacokinetics of the present compounds for maximum beneficial effect in a patient.

E. EXAMPLES

Aspects of the present teachings may be further understood in light of the following examples, which should not be construed as limiting the scope of the present teachings in any way.

Example 1

Coating Nanofiber Scaffolds with Beta Cell Membrane to Promote Cell Proliferation and Function Introduction In this Example, a new and robust strategy in nanofiber scaffold modification to promote cell proliferation and function by coating polymeric nanofibers with the entire functional utility of cell membranes derived directly from natural cells is demonstrated. This work represents the first attempt to investigate the 'coatability' of polymeric nanofibers with natural cell membranes.

This example chose pancreatic beta cell as a model cell line to conduct the study because these cells rely on direct cell-cell interaction to maintain their survival and function,[32, 33] and such characteristics have been explored to design scaffolds aimed to promote beta cell function.[17, 34] Beta cell membrane-coated nanofiber scaffolds possess an antigenic exterior closely resembling that of the source cells, thereby recapitulating the characteristics of intercellular interaction among beta cells found in the pancreas. As illustrated in FIG. 1A, cell membrane-derived vesicles are collected from beta cells and then coated onto polymeric nanofibers. In the study, the successful preparation of cell membrane-coated nanofibers (CM-fibers) was demonsrated and it was validated that the CM-fibers can enhance cell survival and promote cell function when they are used as scaffolds to culture beta cells.

Results and Discussion

Figure 1B:
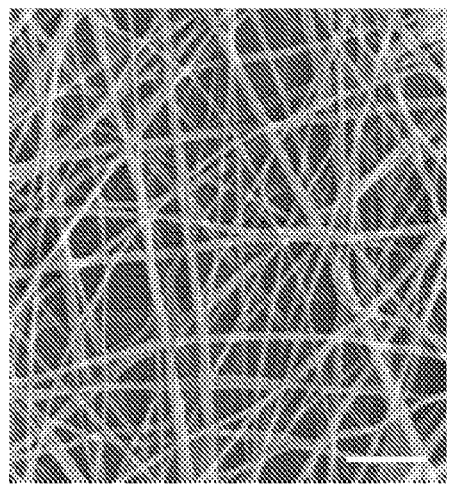
Figure 1C:
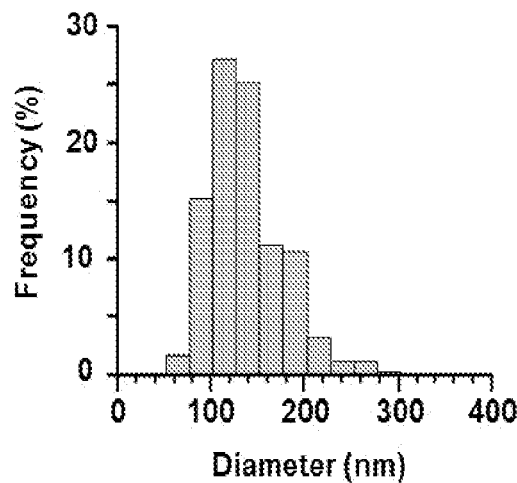

The fabrication of CM-fibers can be divided into three steps (FIG. 1A). The first step was to prepare beta cell membrane-derived vesicles (βC vesicles). Specifically, MIN6 mouse pancreatic cells were used as a model beta cell line to collect cell membrane by emptying intracellular contents through a combination of osmotic lysis, mechanical membrane disruption, and differential centrifugation.[24] The purity of the membrane was confirmed by Western blotting analysis, which showed the absence of nuclear and cytosolic markers. The collected MIN6 cell membrane was then sonicated to generate βC vesicles with an average diameter of 120±5.3 nm. The second step was to produce uncoated nanofibers (Un-fibers). Specifically, polycaprolactone (PCL) was chosen to prepare nonwoven nanofibers through an established electron-spinning process.[35-37] In the study, PCL and poly-$_D$-lysine were dissolved in a formic acid-acetone mixture solution (7:3 v/v) with a final polymer concentration of 10% (w/v) and 1% (w/v), respectively. Then the polymer solution was loaded into a syringe and injected by using a microinjection pump with a 20 kV high voltage applied to the needle. The flow rate of the polymer solution was kept at 0.5 mL/h. The generated nanofibers were collected using glass cover slips mounted on an aluminum foil. In the third step, the polymeric nanofibers were coated with βC vesicles through a fusion process. Freshly prepared βC vesicles were immediately added to the Un-fibers and the two components were allowed to incubate at room temperature for 30 min. After the incubation, the vesicle suspension was removed and the nanofiber sample was washed and dried. When examined with scanning electron microscope (SEM), the CM-fibers showed a smooth outer surface and an overall long fibrous morphology (FIG. 1B). Based on the SEM micrographs, CM-fiber diameter distribution was found in the range of 50-280 nm (FIG. 1C).

To confirm the fusion between βC vesicles and Un-fibers, the cell membrane and the inner aqueous compartment of the βC vesicles were labeled with DiD (excitation/emission=644/665 nm) and calcein-AM (excitation/emission=495/516 nm), respectively. As shown in FIG. 2A, the fluorescence spectrum of these dual-dye labeled βC vesicles display two distinct fluorescence bands characteristic of the signals from the membrane and the inner space. The dual-dye labeled βC vesicles were then incubated with Un-fibers for 30 min, followed by excess washing to remove excess vesicles. Florescent measurement of the resulting CM-fibers showed only red fluorescence signal from the cell membrane while the green fluorescence from the intra-vesicle compartment was largely absent. This observation was further confirmed by examining the fluorescence distribution over the CM-fibers. FIG. 2B shows that the near infrared fluorescence emitted from the cell membrane spread evenly on the nanofibers and the fluorescent pattern matched the long fibrous morphology of the nanofibers. In contrast, the intra-vesicle fluorescence signal was not observed over the CM-fibers. Collectively, these results indicate a uniform membrane coating over the fibers, resulting from an effective vesicle-nanofiber fusion process, in which the vesicles wrap around the nanofibers and release their intra-vesicle content. To further validate the fusion process, non-fusogenic βC vesicles were prepared by pre-coating the vesicles onto poly(lactic-co-glycolic acid) (PLGA) nanoparticle cores, which was labeled with green fluorescent dye Alexa 488 (excitation/emission=495/519 nm), to passivate their fusion ability. The non-fusogenic βC vesicles were then added to the Un-fibers, followed by the same incubation and washing steps as for the fusogenic βC vesicles. Different from the fusogenic vesicles, fluorescence signals corresponding to both the membrane and the core were detected and their intensity ratio remained unchanged after incubation with the Un-fibers (FIG. 2C). Fluorescent images further demonstrated that both fluorescent signals were observed over the fibers and the fluorescent signals exhibited spotty patterns that co-localized with each other on the fibers (FIG. 2D). These results suggest that the non-fusogenic βC vesicles randomly adsorb onto the Un-fibers rather than fusing with the fibers.

Figure 3A:
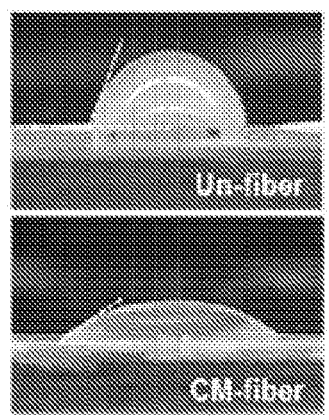
FIGS. 3A-3E show a surface characterization of CM-fibers.
Figure 3B:
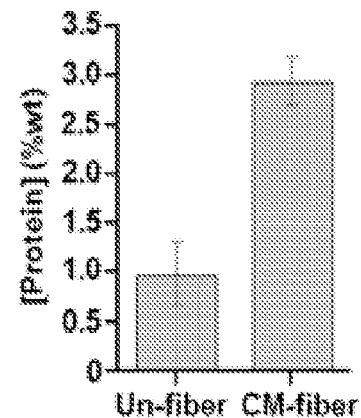
Figure 3C:
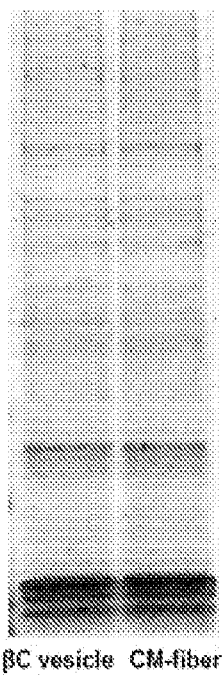
Figure 3D:
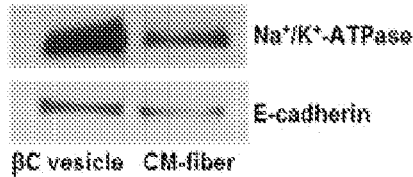
Figure 3E:
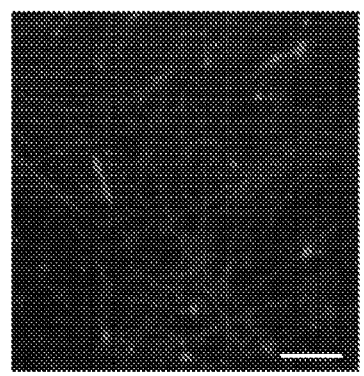

The membrane coating was further verified by examining the surface properties of the CM-fibers. First, the wettability of the CM-fibers was examined by measuring the surface contact angles. Prior to the coating, the static water contact angle of Un-fibers was 69.1±2.7° (FIG. 3A). After cell membrane coating the water contact angle of CM-fibers was 30.9±3.4°. This significant decrease of contact angle indicates that the CM-fibers become more hydrophilic following the coating process and this change in wettability is attributable to the hydrophilic nature of the coated cell membrane. The membrane coating was also verified with a protein bicinchoninic acid (BCA) assay (FIG. 3B). The Un-fibers showed approximately 1 wt % of protein loading yield (defined as the weight ratio of protein content to the nanofibers) due to the addition of poly-$_D$-lysine in the electrospinning process. In contrast, the CM-fibers showed a significantly increased protein loading yield of 2.8±0.5 wt %. Analysis of the protein content on the CM-fibers was also carried out to confirm successful functionalization of the nanofibers with MIN6 cell membrane antigens. CM-fibers were rinsed to remove uncoated vesicles. Gel electrophoresis followed by protein staining showed that the protein profile of the CM-fibers matched closely with that of βC vesicles (FIG. 3C). Western blotting analysis further demonstrated significant enrichment of $Na^+/K^+$-ATPase and E-cadherin, two plasma membrane-specific markers, in the CM-fiber formulation as compared to βC vesicles, suggesting the successful translocation of membrane proteins onto the nanofibers (FIG. 3D). Following the confirmation of its presence on the CM-fibers, E-cadherin was immunostained with a fluorescence dye and examined with fluorescence microscopy. FIG. 3E shows that the protein marker evenly distributed over the long fibrous nanofiber scaffolds. Collectively, these results not only verify successful membrane coating on the nanofibers, but also demonstrate effective retention of membrane antigens on the nanofibers through the preparation process.

Figure 4A:
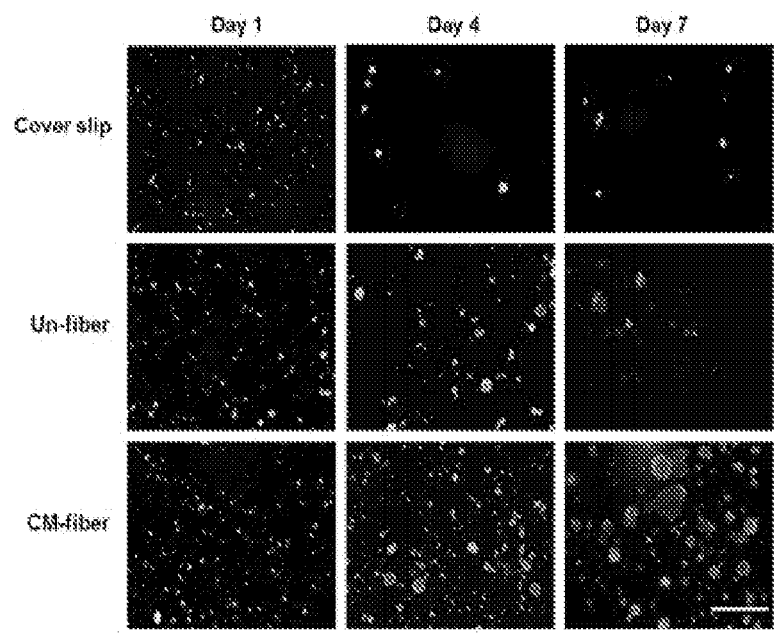
FIGS. 4A-4D show CM-fibers promoting MIN6 cell proliferation and function.

After having evaluated the preparation and characteristics of CM-fibers, the effectiveness of the CM-fibers in promoting beta cell proliferation and function was tested. In the study, MIN6 beta cells were cultured on three different substrates including CM-fibers, Un-fibers, and non-coating cover slips. Cell viability was first tested using a live/dead assay, where live cells were stained with calcein-AM that emits green fluorescence and dead cells with propidium iodide that emits red fluorescence (FIG. 4A). Under the experimental conditions, on day 1, MIN6 cells evenly distributed on all three substrates and no obvious differences in cell viability were observed. On day 4, cells on CM-fibers showed obvious growth and formed small clusters. In contrast, fewer live cells were seen on Un-fibers and even fewer on non-coating cover slips. On day 7, cells on CM-fibers grew into an even higher density and formed large clusters, whereas cells on Un-fibers and cover slips only showed few sporadic, surviving cell clusters.

Figure 4B:
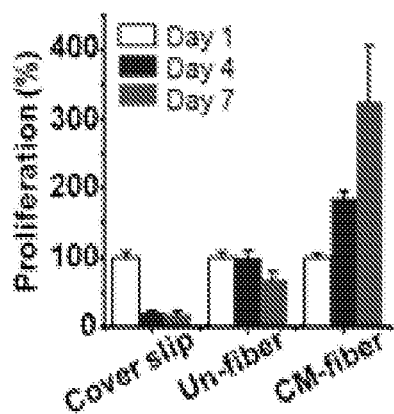
Figure 4C:
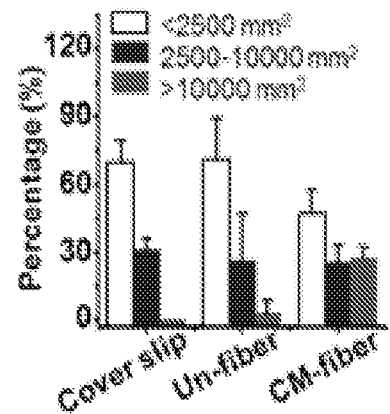

Cell proliferation rate was further quantified based on live/dead assay results (FIG. 4B). On day 4 and 7, the number of live cells on CM-fibers increased to 186% and 327%, respectively, as compared to the number on day 1. However, such number dropped to 67% and 18% for cells cultured on Un-fibers and non-coating cover slips, respectively, on day 7. FIG. 4C shows the size distribution of MIN6 cell clusters on day 7. The cluster sizes were divided into three categories: <2500 $mm^2$, 2500-10000 $mm^2$, and >10000 $mm^2$. For CM-fibers the size distribution of cell clusters in the three size categories were 47%, 26% and 27%, respectively. For both Un-fibers and non-coating cover slips, about 70% of cell clusters were below 2500 $mm^2$, while no more than 3% of cell clusters were larger than 10000 $mm^2$. Therefore, MIN6 cells cultured on CM-fibers have the highest proliferative rate and tend to form larger cell clusters as compared to the control groups.

Figure 4D:
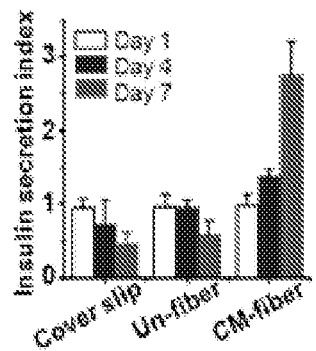

Finally, the insulin secretion index for MIN6 cells cultured on the three different substrates was monitored. Previous studies have shown that cell-cell contact is critical in maintaining glucose-responsive insulin secretion from MIN6 cell.[38] Especially, cells encapsulated at higher cell-packing densities secreted larger amounts of insulin upon glucose stimulation.[17, 39] In the study, the amount of insulin secreted under 25 mM glucose was normalized to insulin secreted under 2.5 mM glucose, and the ratio is defined as insulin secretion index. Such index of cells cultured on the three different substrates was measured on day 1, 4, and 7. As shown in FIG. 4D, cells cultured on CM-fibers had an insulin secretion index of 0.97±0.15, 1.37±0.09, and 2.76±0.45 on day 1, 4, and 7, respectively. In contrast, the insulin secretion index of MIN6 cells cultured on Un-fibers (0.96±0.17, 0.96±0.09, and 0.58±0.18 on day 1, 4, and 7, respectively) and cover slips (0.94±0.12, 0.72±0.34, and 0.46±0.15 on day 1, 4, and 7, respectively) decreased with time. These results clearly show that MIN6 cell membrane coating not only promotes the survival of dispersed MIN6 cells in the nanofiber scaffolds, but also enhances the glucose-dependent insulin secretion from the cells.

Conclusions

A new and facile approach to functionalizing nanofiber scaffolds to promote cell proliferation and function by coating polymeric nanofibers with the entire functional utility of natural cell membrane has been developed. Using pancreatic beta cell as a model cell line, the preparation process and validated successful coating of beta cell membrane onto the surface of polymeric nanofibers was demonstrated. The resulting cell membrane-coated nanofibers retained the dimensional and physical properties of uncoated nanofibers while possessing an antigenic exterior closely resembling that of the source beta cell. When seeding beta cells in such modified nanofiber scaffolds, the cell membrane coating provided a natural environment recapitulating the cell-cell interaction among beta cells in the pancreas and thus promoted cell survival and function. Specifically, it significantly enhanced glucose-dependent insulin secretion from the cultured beta cells. Since the initial report on cell membrane cloaking technique,[22] it has been applied to coat a wide range of synthetic spherical nanoparticles and the resulting biomimetic nanoparticles have demonstrated a versatile therapeutic applications. This work successfully extends the cell membrane cloaking technique from spherical nanoparticles to long nanofibers, which represents a whole new class of nanomaterials marked with drastic differences in material dimensionality, physicochemical properties, and applications. Cell membrane-coated nanofibers are expected to add additional flexibility and controllability in harnessing cell membrane functions, and open unique opportunities for innovative applications.

Materials and Methods

MIN6 cell culture and membrane derivation. A mouse pancreatic beta cell line, MIN6, was obtained from AddexBio Technologies (San Diego, Calif.) and cultured in Dulbecco's Modified Eagle Medium (DMEM, Invitrogen) supplemented with 10% v/v fetal bovine serum (FBS, Hyclone) and 1% v/v penicillin-streptomycin (Invitrogen). Cell membrane was harvested by following a previously published protocol[24]. Specifically, MIN6 cells were grown in T-175 culture flasks to full confluency and detached by scrapping the culture flask surfaces. Washed cells were suspended in a hypotonic lysing buffer containing 20 mM Tris-HCl (pH=7.5), 10 mM KCl, 2 mM $MgCl_2$, and 1 EDTA-free mini protease inhibitor tablet (Pierce), and then disrupted using a dounce homogenizer with a tight-fitting pestle. The cell suspension was subjected to 20 passes and then centrifuged at 20,000×g for 20 mM, after which the pellet was discarded. The collected supernatant was centrifuged again at 100,000×g for 45 min, and the pellet was collected and used as purified MIN6 cell membrane for subsequent experiments.

Synthesis of polycaprolactone nanofibers. Polycaprolactone (PCL, $M_w$=70-90 KDa, Sigma-Aldrich) and poly-$_D$-lysine ($M_w$=30-70 KDa, Sigma-Aldrich) were dissolved in a formic acid-acetone mixture solution (7:3 v/v) with a final polymer concentration of 10% (w/v) and 1% (w/v), respectively. The polymer solution was loaded into a 10 mL syringe with a gauge 23 needle, which was then placed onto a microinjection pump (New Era Pump Systems Inc). To inject the polymer solution, a 20 kV high voltage (Gamma High Voltage Research) was applied to the needle and the flow rate of the solution was 0.5 mL/h. To collect the nanofibers, a glass cover slip (0.15 mm in thickness, VWR) was cut into 4×4 mm square pieces and taped onto a large piece of aluminum foil, which served as a collector and was connected to the ground. The distance between the needle and the aluminum foil collector was 10 cm.

Coating nanofibers with MIN6 cell membrane. The collected MIN6 cell membrane was sonicated with an FS30D bath sonicator (Fisher Scientic) at a frequency of 42 kHz and a power of 100 W. The sonication lasted 3 min to form beta cell membrane-derived vesicles (denoted βC vesicles). Immediately following the sonication, the nanofibers cast on the glass cover slip were immersed into the βC vesicle suspension and kept for 30 min at room temperature. Then the solution was discarded and the nanofibers were rinsed with deionized water. After drying in air, the morphology and the thickness of the cell membrane-coated nanofibers (denoted CM-fibers) were examined by scanning electron microscopy (SEM). Nanofiber diameter and size distribution were obtained by measuring diameters of 100 CM-fibers randomly selected from five independent samples.

βC vesicle-nanofiber fusion study. To study and verify the fusion between βC vesicles and the nanofibers, βC vesicles were fluorescently labeled with 1,1'-dioctadecyl-3,3,3',3'-tetramethylindodicarbocyanine perchlorate (DiD; excitation/emission=644/665 nm; Life Technologies) into the cell membrane and calcein-AM (excitation/emission=495/516 nm; eBioscience) into the inner aqueous compartment of the vesicles, respectively. Specifically, DiD was first mixed with a trivial amount of egg PC in chloroform (approximately DiD:egg PC=1:9, molar ratio), and then dried by flowing nitrogen gas over the sample. To the dried film, calcein-AM solution and MIN6 cell membrane were added. The mixture was sonicated with an FS30D bath sonicator (Fisher Scientic) at a frequency of 42 kHz and a power of 100 W for 3 min to form fluorescently labelled βC vesicles. The fusogenic βC vesicles were then incubated with the nanofibers at room temperature for 30 min. The resulting CM-fibers were rinsed and imaged with an EVOS® inverted fluorescence microscope (Thermo Fisher Scientific). The fluorescence intensity was quantified with a microplate reader (BioTek Instruments). To prepare non-fusogenic βC vesicles as a control group, poly(lactic-co-glycolic acid) (PLGA) polymeric cores with a diameter of ~100 nm were prepared using 0.67 dL/g of carboxy-terminated 50:50 PLGA(LACTEL Absorbable Polymers) through a nanoprecipitation process.[22] For fluorescent labeling of the polymeric cores, Alexa 488 (excitation/emission=495/519 nm; Life Technology) was covalently conjugated to about 5% of the PLGA polymers that form the cores. Finally, the DiD-labeled βC vesicles were coated onto the Alexa 488-labeled polymeric cores following a previously published protocol[29]. The nanoparticle-supported cell membrane would lose its fusion activity[23, 28] and thus can serve as a non-fusogenic control of the fusogenic βC vesicles.

Protein analysis of CM-fibers. For protein characterization using sodium dodecyl sulfate polyacrylamide gel electrophoresis, all samples were prepared at a final protein concentration of 1 mg/mL in lithium dodecyl sulfate (LDS) loading buffer (Invitrogen) as measured by a BCA assay (Pierce). CM-fibers were rinsed in PBS and then disintegrated via soncation using a FS30D bath sonicator at a frequency of 42 kHz and a power of 100 W for 5 min. Samples were heated at 70° C. for 10 min and 20 μL was loaded into each well of a NuPAGE Novex 4-12% Bis-Tris 10-well minigel (Invitrogen) in MOPS running buffer (Invitrogen) in an XCell SureLock Electrophoresis System (Invitrogen) following manufacturer's instructions. Protein staining was accomplished using SimplyBlue (Invitrogen) and destained in water overnight before imaging. For western blot analysis, protein was transferred to Protran nitrocellulose membranes (Whatman) using an XCell II Blot Module (Invitrogen) in NuPAGE transfer buffer (Invitrogen) following manufacturer's instructions. Membrane proteins were probed using antibodies against E-cadherin (147301, Biolegend) and $Na^+/K^+$-ATPase (A01483, GenScript) along with horseradish peroxidase (HRP)-conjugated anti-mouse IgG (Poly4053, Biolegend). Films were developed using ECL western blotting substrate (Pierce) and developed with the Mini-Medical/90 Developer (ImageWorks).

MIN6 cell aggregation and proliferation on CM-fibers. To analyze the cell-cell aggregates, CM-fibers on glass cover slips were placed into the wells of 96-well microplates (Corning). To each well, approximately $1 \times 10^4$ MIN6 cells were seeded and cultured in DMEM medium containing 15% v/v FBS and 1% v/v penicillin-streptomycin. Uncoated nanofibers (Un-fibers) and bare glass cover slips were used as control groups. On day 1, 4, and 7, samples were treated with calcein-AM and PI (Thermo Fisher Scientific) to label the live and dead cells, respectively. For labeling, the cell culture medium in the plate was removed and then 200 μL PBS containing 3 mM Calcein-AM and 10 mM PI was added to each well. The plate was incubated under culture conditions for 30 min and imaged with an EVOS® inverted fluorescence microscope (Thermo Fisher Scientific). The size and size distribution of the MIN6 cell aggregates were quantified using ImageJ software. The results shown were representative images of at least independent samples. For MIN6 proliferation study, the cell number was quantified by measuring the fluorescent signal with an excitation wavelength of 485 nm and emission wavelength of 530 nm. All experiments were repeated at least three times.

Insulin secretion study. The glucose-stimulated insulin secretion from MIN6 cells were measured following a previously reported method[34]. Briefly, MIN6 cells cultured on CM-fibers, Un-fibers, or bare glass cover slips were pre-incubated in the Krebs Ringer HEPES (KRBH) buffer solution at 37° C. for 45 min. Then MIN6 cells were incubated in KRBH buffer containing 2.5 mM glucose for 1 hour and the supernatant was collected. Subsequently, the cells were incubated in KRBH buffer containing 25 mM glucose for another 1 hour and the supernatant was collected. The insulin concentration in the collected supernatants was quantified with mouse Insulin ELISA kit (Mercodia Inc) following manufacturer's instructions. The amount of insulin secreted under 25 mM glucose was normalized to insulin secreted under 2.5 mM glucose, which defines the insulin secretion index used in this study. Statistical analysis was performed with a two-tailed, unpaired Student's t-test.

REFERENCES

1. Stevens, M. M.; George, J. H. *Science* 2005, 310 (5751), 1135-8.
2. Dvir, T.; Timko, B. P.; Kohane, D. S.; Langer, R. *Nat. Nanotechnol.* 2011, 6 (1), 13-22.
3. Liu, X. L.; Wang, S. T. *Chem. Soc. Rev.* 2014, 43 (8), 2385-401.
4. Freed, L. E.; Engelmayr, G. C., Jr.; Borenstein, J. T.; Moutos, F. T.; Guilak, F. *Adv. Mater.* 2009, 21 (32-33), 3410-8.
5. Vogel, V.; Sheetz, M. *Nat. Rev. Mol. Cell Biol.* 2006, 7 (4), 265-75.
6. Fisher, O. Z.; Khademhosseini, A.; Langer, R.; Peppas, N. A. *Acc. Chem. Res.* 2010, 43 (3), 419-28.
7. Liu, X.; Holzwarth, J. M.; Ma, P. X. *Macromol. Biosci.* 2012, 12 (7), 911-9.
8. Tamayol, A.; Akbari, M.; Annabi, N.; Paul, A.; Khademhosseini, A.; Juncker, D. *Biotechnol. Adv.* 2013, 31 (5), 669-87.
9. Tallawi, M.; Rosellini, E.; Barbani, N.; Cascone, M. G.; Rai, R.; Saint-Pierre, G.; Boccaccini, A. R. *J. R. Soc. Interface* 2015, 12 (108).
10. Zhang, Z.; Gupte, M. J.; Jin, X.; Ma, P. X. *Adv. Funct. Mater.* 2015, 25 (3), 350-60.
11. South, C. R.; Burd, C.; Weck, M. *Acc. Chem. Res.* 2007, 40 (1), 63-74.
12. Lin, C.-C.; Anseth, K. S. *Adv. Funct. Mater.* 2009, 19 (14), 2325-31.
13. Hudalla, G. A.; Murphy, W. L. *Adv. Funct. Mater.* 2011, 21 (10), 1754-68.
14. Hume, P. S.; Anseth, K. S. *Biomaterials* 2010, 31 (12), 3166-74.
15. Yue, X.-S.; Murakami, Y.; Tamai, T.; Nagaoka, M.; Cho, C.-S.; Ito, Y.; Akaike, T. *Biomaterials* 2010, 31 (20), 5287-96.
16. Moon, J. J.; Lee, S.-H.; West, J. L. *Biomacromolecules* 2007, 8 (1), 42-9.
17. Lin, C.-C.; Anseth, K. S. *Proc. Natl. Acad. Sci. U.S.A.* 2011, 108 (16), 6380-5.
18. Tian, B.; Cohen-Karni, T.; Qing, Q.; Duan, X.; Xie, P.; Lieber, C. M. *Science* 2010, 329 (5993), 830-4.
19. Tunuguntla, R. H.; Bangar, M. A.; Kim, K.; Stroeve, P.; Grigoropoulos, C.; Ajo-Franklin, C. M.; Noy, A. *Adv. Mater.* 2015, 27 (5), 831-6.
20. Williams, D. F. *Biomaterials* 2009, 30 (30), 5897-909.
21. Rice, J. J.; Martino, M. M.; De Laporte, L.; Tortelli, F.; Briquez, P. S.; Hubbell, J. A. *Adv. Healthc. Mater.* 2013, 2 (1), 57-71.
22. Hu, C.-M. J.; Zhang, L.; Aryal, S.; Cheung, C.; Fang, R. H.; Zhang, L. *Proc. Natl. Acad. Sci. U.S.A.* 2011, 108 (27), 10980-5.
23. Hu, C.-M. J.; Fang, R. H.; Copp, J.; Luk, B. T.; Zhang, L. *Nat. Nanotechnol.* 2013, 8 (5), 336-40.
24. Fang, R. H.; Hu, C.-M. J.; Luk, B. T.; Gao, W.; Copp, J. A.; Tai, Y.; O'Connor, D. E.; Zhang, L. *Nano Lett.* 2014, 14 (4), 2181-8.
25. Gao, W.; Fang, R. H.; Thamphiwatana, S.; Luk, B. T.; Li, J.; Angsantikul, P.; Zhang, Q.; Hu, C.-M. J.; Zhang, L. *Nano Lett.* 2015, 15 (2), 1403-9.
26. Hu, C.-M. J.; Fang, R. H.; Wang, K.-C.; Luk, B. T.; Thamphiwatana, S.; Dehaini, D.; Nguyen, P.; Angsantikul, P.; Wen, C. H.; Kroll, A. V.; Carpenter, C.; Ramesh, M.; Qu, V.; Patel, S. H.; Zhu, J.; Shi, W.; Hofman, F. M.; Chen, T. C.; Gao, W.; Zhang, K.; Chien, S.; Zhang, L. *Nature* 2015, 526 (7571), 118-21.
27. Parodi, A.; Quattrocchi, N.; van de Ven, A. L.; Chiappini, C.; Evangelopoulos, M.; Martinez, J. O.; Brown, B. S.; Khaled, S. Z.; Yazdi, I. K.; Vittoria Enzo, M.; Isenhart, L.; Ferrari, M.; Tasciotti, E. *Nat. Nanotechnol.* 2013, 8 (1), 61-8.
28. Hu, C.-M. J.; Fang, R. H.; Luk, B. T.; Zhang, L. *Nat. Nanotechnol.* 2013, 8 (12), 933-8.
29. Copp, J. A.; Fang, R. H.; Luk, B. T.; Hu, C.-M. J.; Gao, W.; Zhang, K.; Zhang, L. *Proc. Natl. Acad. Sci. U.S.A.* 2014, 111 (37), 13481-6.
30. Ding, H.; Lv, Y.; Ni, D.; Wang, J.; Tian, Z.; Wei, W.; Ma, G. *Nanoscale* 2015, 7 (21), 9806-15.
31. Pang, Z.; Hu, C.-M. J.; Fang, R. H.; Luk, B. T.; Gao, W.; Wang, F.; Chuluun, E.; Angsantikul, P.; Thamphiwatana, S.; Lu, W.; Jiang, X.; Zhang, L. *Acs Nano* 2015, 9 (6), 6450-8.
32. Luther, M. J.; Davies, E.; Muller, D.; Harrison, M.; Bone, A. J.; Persaud, S. J.; Jones, P. M. *Am. J. Physiol. Endocrinol. Metabol.* 2005, 288 (3), E502-E9.
33. Konstantinova, I.; Nikolova, G.; Ohara-Imaizumi, M.; Meda, P.; Kucera, T.; Zarbalis, K.; Wurst, W.; Nagamatsu, S.; Lammert, E. *Cell* 2007, 129 (2), 359-70.
34. Li, W.; Lee, S.; Ma, M.; Kim, S. M.; Guye, P.; Pancoast, J. R.; Anderson, D. G.; Weiss, R.; Lee, R. T.; Hammond, P. T. *Sci. Rep.* 2013, 3, Article number: 2863.
35. Lalani, R.; Liu, L. *Biomacromolecules* 2012, 13 (6), 1853-1863.

36. Eslami, M.; Vrana, N. E.; Zorlutuna, P.; Sant, S.; Jung, S.; Masoumi, N.; Khavari-Nejad, R. A.; Javadi, G.; Khademhosseini, A. *J. Biomater. Appl.* 2014, 29 (3), 399-410.
37. Chew, S. Y.; Mi, R.; Hoke, A.; Leong, K. W. *Biomaterials* 2008, 29 (6), 653-61.
38. Parnaud, G.; Lavallard, V.; Bedat, B.; Matthey-Doret, D.; Morel, P.; Berney, T.; Bosco, D. *Diabetes* 2015, 64 (3), 887-96.
39. Blackstone, B. N.; Palmer, A. F.; Rilo, H. R.; Powell, H. M. *Tissue Eng. Part A* 2014, 20 (13-14), 1784-93.

What is claimed is:
1. A nanostructure comprising:
   a) an inner core comprising a non-cellular or non-viral material; and
   b) an outer surface comprising a membrane derived from a cell,
      wherein said nanostructure has a first dimension ranging from about 1 nm to about 10 µm, a second dimension at least about 11 µm, and a ratio between said second dimension and said first dimension of at least about 2,
   wherein the membrane is derived from a cell in a tissue selected from the group consisting of a connective tissue, a blood, a bone, a tendon, a ligament, an adipose, an areolar tissue, a muscle tissue, a smooth muscle, a skeletal muscle, a cardiac muscle (heart muscle), a nervous tissue, a tissue of central nervous system (CNS), brain, spinal cord, peripheral nervous system (PNS), a cranial nerve, a spinal nerve, an epithelial tissue, simple squamous epithelium, stratified squamous epithelium, simple cuboidal epithelium, transitional epithelium, pseudostratified columnar epithelium (AKA ciliated columnar epithelium), columnar epithelium, glandular epithelium, and ciliated columnar epithelium, and
   wherein the nanostructure substantially lacks constituents of the cell from which the membrane is derived.
2. The nanostructure of claim 1, wherein the non-cellular or non-viral material comprises a polymer.
3. The nanostructure of claim 2, wherein the polymer comprises poly(lactic-co-glycolic acid) (PLGA), polylactic acid (PLA), poly(l-lactic acid) (PLLA), polyglycolic acid (PGA), polycaprolactone (PCL), polylysine, polyglutamic acid, poly(ethylene-co-vinyl acetate) (EVOH), poly(vinyl acetate) (PVA), polyethylene glycol (PEG), poly(glycerol sebacate) (PGS), polydioxanone (PDO), polyphosphazenes, polyurethane (PU), or a combination thereof.
4. The nanostructure of claim 1, wherein the inner core supports the outer surface.
5. The nanostructure of claim 1, wherein the cell is a human cell.
6. The nanostructure of claim 1, wherein the membrane is derived from a cell of an organ system.
7. The nanostructure of claim 1, which further comprises a releasable cargo.
8. The nanostructure of claim 1, wherein the inner core comprises PCL and the outer surface comprises a plasma membrane derived from a β cell.
9. The nanostructure of claim 1, wherein the nanostructure substantially lacks immunogenicity to a species or subject from which the membrane is derived.
10. The nanostructure of claim 1, which is configured as a nanofiber, nanotube or nanowire.
11. The nanostructure of claim 1, which is configured as a nanosheet.
12. A method of treating a disease or condition in a subject comprising administering to a subject in need thereof a treatment effective amount of a nanostructure comprising:
   a) an inner core comprising a non-cellular or non-viral material; and
   b) an outer surface comprising a membrane derived from a cell,
      wherein said nanostructure has a first dimension ranging from about 1 nm to about 10 µm, a second dimension at least about 11 µm, and a ratio between said second dimension and said first dimension of at least about 2,
   wherein the membrane is derived from a cell in a tissue selected from the group consisting of a connective tissue, a blood, a bone, a tendon, a ligament, an adipose, an areolar tissue, a muscle tissue, a smooth muscle, a skeletal muscle, a cardiac muscle (heart muscle), a nervous tissue, a tissue of central nervous system (CNS), brain, spinal cord, peripheral nervous system (PNS), a cranial nerve, a spinal nerve, an epithelial tissue, simple squamous epithelium, stratified squamous epithelium, simple cuboidal epithelium, transitional epithelium, pseudostratified columnar epithelium (AKA ciliated columnar epithelium), columnar epithelium, glandular epithelium, and ciliated columnar epithelium, and
   wherein the nanostructure substantially lacks constituents of the cell from which the membrane is derived.
13. The method of claim 12, wherein the disease or condition is selected from the group consisting of an infectious disease, a parasitic disease, a neoplasm, a cancer, a disease of the blood and blood-forming organs, a disorder involving the immune mechanism, endocrine, nutritional and metabolic diseases, a mental and behavioral disorder, a disease of the nervous system, a disease of the eye and adnexam, a disease of the ear and mastoid process, a disease of the circulatory system, a disease of the respiratory system, a disease of the digestive system, a disease of the skin and subcutaneous tissue, a disease of the musculoskeletal system and connective tissue, a disease of the genitourinary system, pregnancy, childbirth and the puerperium, a condition originating in the perinatal period, a congenital malformation, a deformation, a chromosomal abnormality, an injury, a poisoning, a consequence of external causes, and an external cause of morbidity and mortality.
14. The method of claim 12, wherein the cellular membrane in the nanostructure is derived from a cell of the same species of the subject or is derived from a cell of the subject.
15. The method of claim 12, wherein the cellular membrane in the nanostructure is derived from a red blood cell of the same species of the subject and the red blood cell has the same blood type of the subject.
16. A method to anchor and/or grow a target cell, which method comprises contacting a target cell with a nanostructure under conditions that allow said target cell to anchor on or attach to said nanostructure and/or grow,
   wherein said nanostructure comprises an inner core comprising a non-cellular material and an outer surface comprising a cellular membrane derived from a source cell,
   wherein said cellular membrane derived from said source cell allows said target cell to anchor on or attach to said nanostructure,
wherein said nanostructure has a first dimension ranging from about 1 nm to about 10 µm, a second dimension at least about 11 µm, and a ratio between said second dimension and said first dimension of at least about 2, and wherein the membrane is derived from a source cell in a tissue selected from the group consisting of a connective tissue, a blood, a bone, a tendon, a ligament, an adipose, an areolar tissue, a muscle tissue, a smooth muscle, a skeletal muscle, a cardiac muscle (heart muscle), a nervous tissue, a tissue of central nervous system (CNS), brain, spinal cord, peripheral nervous system (PNS), a cranial nerve, a spinal nerve, an epithelial tissue, simple squamous epithelium, stratified squamous epithelium, simple cuboidal epithelium, transitional epithelium, pseudostratified columnar epithelium (AKA ciliated columnar epithelium), columnar epithelium, glandular epithelium, and ciliated columnar epithelium, and wherein the nanostructure substantially lacks constituents of the cell from which the membrane is derived.

* * * * *